US011739350B2

(12) United States Patent
Ilkow et al.

(10) Patent No.: US 11,739,350 B2
(45) Date of Patent: Aug. 29, 2023

(54) MICRORNA-BASED COMPOSITIONS AND METHODS USED IN DISEASE TREATMENT

(71) Applicant: Ottawa Hospital Research Institute, Ottawa (CA)

(72) Inventors: Carolina Solange Ilkow, Ottawa (CA); John Cameron Bell, Ottawa (CA); Victoria Ann Maher, Leeds (GB); Briana Livia Rollande Samson, Morriston (CA)

(73) Assignee: OTTAWA HOSPITAL RESEARCH INSTITUTE, Ottawa (CA)

( * ) Notice: Subject to any disclaimer, the term of this patent is extended or adjusted under 35 U.S.C. 154(b) by 0 days.

(21) Appl. No.: 17/046,124

(22) PCT Filed: Apr. 10, 2019

(86) PCT No.: PCT/CA2019/050438
§ 371 (c)(1),
(2) Date: Oct. 8, 2020

(87) PCT Pub. No.: WO2019/195936
PCT Pub. Date: Oct. 17, 2019

(65) Prior Publication Data
US 2021/0032662 A1    Feb. 4, 2021

Related U.S. Application Data

(60) Provisional application No. 62/655,585, filed on Apr. 10, 2018.

(51) Int. Cl.
*C12N 15/113*    (2010.01)
*C12N 15/87*     (2006.01)
*C12N 7/00*      (2006.01)

(52) U.S. Cl.
CPC ............... *C12N 15/87* (2013.01); *C12N 7/00* (2013.01); *C12N 15/113* (2013.01);
(Continued)

(58) Field of Classification Search
CPC ........ C12N 15/87; C12N 7/00; C12N 15/113; C12N 2310/141; C12N 2310/531; C12N 2320/32
See application file for complete search history.

(56) References Cited

U.S. PATENT DOCUMENTS

| 8,993,532 B2 | 3/2015 | Hannon et al. |
| 2015/0197749 A1 | 7/2015 | Hannon et al. |
| 2017/0342410 A1 | 11/2017 | Hannon et al. |

FOREIGN PATENT DOCUMENTS

| WO | 2006110688 A2 | 10/2006 |
| WO | 2012015775 A2 | 2/2012 |

(Continued)

OTHER PUBLICATIONS

Navqi et al. (Frontiers in Immunology (Mar. 6, 2018) 9:433, pp. 1-16). (Year: 2018).*

(Continued)

*Primary Examiner* — J. E. Angell
(74) *Attorney, Agent, or Firm* — Borden Ladner Gervais LLP; David Nauman

(57) ABSTRACT

The present disclosure provides a miRNA hairpin that, when processed by a virus-infected cell, increases the therapeutic effectiveness of the virus. The present disclosure also provides a virus encoding such a miRNA hairpin. The present disclosure also provides pre-miRNAs that, when processed by a virus-infected cell, increase extracellular vesicle secretion of the encoded miRNA hairpin by the virus-infected cell.

Figure 3:
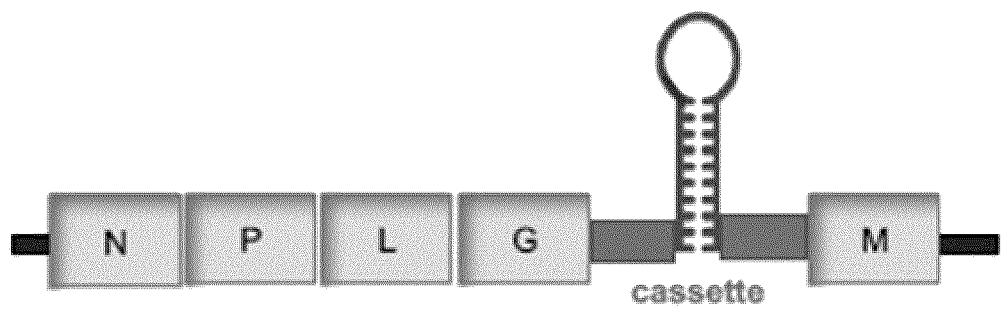

2 Claims, 5 Drawing Sheets
Specification includes a Sequence Listing.

(52) U.S. Cl.
CPC .. *C12N 2310/141* (2013.01); *C12N 2310/531* (2013.01); *C12N 2320/32* (2013.01)

(56) References Cited

FOREIGN PATENT DOCUMENTS

| | | |
|---|---|---|
| WO | 2012044620 A2 | 4/2012 |
| WO | 2017054085 A1 | 4/2017 |
| WO | 2017132552 A1 | 8/2017 |
| WO | 2018045250 A1 | 3/2018 |
| WO | 2018213412 A1 | 11/2018 |

OTHER PUBLICATIONS

Aguado, et al., "MicroRNA Function is Limited to Cytokine Control in the Acute Response to Virus Infection," Cell Host & Microbe, Dec. 2015, vol. 18 (6), pp. 714-722.
Bitler, et al., "Synthetic Lethality by Targeting EZH2 Methyltransferase Activity in Arid1a-mutated Cancers," Nature Medicine, Mar. 2015, vol. 21 (3), pp. 231-238.
Borden, et al., "Transient Introduction of miR-294 in the Heart Promotes Cardiomyocyte Cell Cycle Reentry After Injury," Circulation Research, Apr. 2019, vol. 125 (1), pp. 14-25.
Chang, et al., "Creating an MiR30-based ShRNA Vector," Cold Spring Harbor Protocols, Jul. 2013, vol. 7, pp. 631-635.
Chen, et al., "In Vivo Delivery of MiRNAS for Cancer Therapy: Challenges and Strategies, "Advanced Drug Delivery Reviews, Jan. 2015, vol. 81, pp. 128-141.
Choi, et al., "Multiplexing Seven MiRNA-based ShRNAS to Suppress HIV Replication, "Molecular Therapy : the Journal of the American Society of Gene Therapy, Feb. 2015, vol. 23 (2), pp. 310-320.
Edge, et al., "A Let-7 MicroRNA-sensitive Vesicular Stomatitis Virus Demonstrates Tumor-specific Replication," Molecular Therapy, Aug. 2008, vol. 16 (8), pp. 1437-1443.
European Patent Application No. 19784586.0, Extended European Search Report dated Mar. 5, 2022.
European Patent Application No. 19784586.0, Partial Supplementary European Search Report dated Feb. 1, 2022.
Falcone, et al., "Signaling by Exosomal MicroRNAS in Cancer," Journal of Experimental & Clinical Cancer Research, Dec. 2015, vol. 34 (1), pp. 1-10.
Lang, et al., "Mesenchymal Stem Cells as Natural Biofactories for Exosomes Carrying Mir-124a in the Treatment of Gliomas," Neuro-Oncology, Feb. 2018, vol. 20 (3), pp. 380-390.
Guduric-Fuchs, et al., "Selective Extracellular Vesicle-mediated Export of an Overlapping Set of Micromas From Multiple Cell Types," BMC Genomics, Dec. 2012, vol. 13 (357), pp. 1-14.
Grössl, et al., "A Novel Artificial Microma Expressing AAV Vector for Phospholamban Silencing in Cardiomyocytes Improves Ca2+ Uptake Into the Sarcoplasmic Reticulum," PloS one, Mar. 2014, vol. 9 (3), pp. 1-13.
Guse, et al., "Oncolytic Vaccinia Virus for the Treatment of Cancer," Expert Opinion on Biological Therapy, Feb. 2011, vol. 11 (5), pp. 595-608.
Haney, et al., "Exosomes as Drug Delivery Vehicles for Parkinson's Disease Therapy," Journal of Controlled Release, Mar. 2015, vol. 207, pp. 18-30.
Langlois, et al., "In Vivo Delivery of Cytoplasmic RNA Virus-derived MiRNAs," Molecular Therapy, Feb. 2012, vol. 20 (2), pp. 367-375.
Lei, et al., "Combined Expression of MIR-34a and Smac Mediated by Oncolytic Vaccinia Virus Synergistically Promote Anti-tumor Effects in Multiple Myeloma," Scientific Reports, Aug. 2016, vol. 6 (1), pp. 1-11.
Pegtel, et al., "Functional Delivery of Viral MiRNAS via Exosomes," Proceedings of the National Academy of Sciences of the United States of America, Apr. 2010, vol. 107 (14), pp. 6328-6333.
Pikor, et al., "Oncolytic Viruses: Exploiting Cancer's Deal With the Devil," Trends in Cancer, Dec. 2015, vol. 1 (4), pp. 1-12.
Rehman, et al., "Into the Clinic: Talimogene Laherparepvec (T-VEC), a First-in-class Intratumoral Oncolytic Viral Therapy," Journal for Immunotherapy of Cancer, Sep. 2016, vol. 4 (53), pp. 1-8.
Roden, et al., "Novel Determinants of Mammalian Primary Microma Processing Revealed by Systematic Evaluation of Hairpin-containing Transcripts and Human Genetic Variation," Genome Research, Mar. 2017, vol. 27 (3), pp. 374-384.
Rupaimoole, et al., "Microrna Therapeutics: Towards a New Era for the Management of Cancer and Other Diseases," Nature Reviews: Drug Discovery, Mar. 2017, vol. 16 (3), pp. 203-222.
Stojdl et al., "VSV Strains With Defects in Their Ability to Shutdown Innate Immunity Are Potent Systemic Anti-cancer Agents," Cancer Cell, Oct. 2003, vol. 4 (4), pp. 263-275.
Varble, et al., "An in Vivo RNAi Screening Approach to Identify Host Determinants of Virus Replication," Cell Host & Microbe, Sep. 2013, vol. 14 (3), pp. 346-356.
Varble, et al., "Engineered RNA Viral Synthesis of MicroRNAS," Proceedings of the National Academy of Sciences of the United States of America, Jun. 2010, vol. 107 (25), pp. 11519-11524.
Villarroya-Beltri, et al., "Sumoylated HnRNPA2B1 Controls the Sorting of Mimas Into Exosomes Through Binding to Specific Motifs," Nature Communications, Dec. 2013, vol. 4 (1), pp. 1-10.
Wang, et al., "Widespread Spinal Cord Transduction by Intrathecal Injection of Raav Delivers Efficacious Rnai Therapy for Amyotrophic Lateral Sclerosis," Human Molecular Genetics, Feb. 2014, vol. 23 (3), pp. 668-681.
Wheatley, et al., "Co-expression of MiRNATargeting the Expression of Perk, but Not Pkr, Enhances Cellular Immunity From an Hiv-1 Env Dna Vaccine," PloS One, Mar. 2011, vol. 6 (3), pp. 1-12.
Zhang, et al., "Exosome and exosomal microRNA: trafficking, sorting, and function," Genomics, Proteomics & Bioinformatics, Feb. 2015, vol. 13, pp. 17-24.
Zomer, et al., "Exosomes: Fit to Deliver Small RNA," Communicative & Integrative Biology, Sep. 2010, vol. 3 (5), pp. 447-450.
International Application No. PCT/CA2019/050438, Written Opinion and International Search Report dated Jul. 12, 2019.

* cited by examiner

Fig. 1

Fig. 2

SEQUENCE LISTING

<160> NUMBER OF SEQ ID NOS: 207

<210> SEQ ID NO 1
<211> LENGTH: 22
<212> TYPE: DNA
<213> ORGANISM: Artificial Sequence
<220> FEATURE:
<223> OTHER INFORMATION: Artificial sequence invented by inventors

<400> SEQUENCE: 1
accaacatgt ctcttctcct at                                        22

<210> SEQ ID NO 2
<211> LENGTH: 22
<212> TYPE: DNA
<213> ORGANISM: Artificial Sequence
<220> FEATURE:
<223> OTHER INFORMATION: Artificial sequence invented by inventors

<400> SEQUENCE: 2
ataggagaag agacatgttg gt                                        22

<210> SEQ ID NO 3
<211> LENGTH: 22
<212> TYPE: DNA
<213> ORGANISM: Artificial Sequence
<220> FEATURE:
<223> OTHER INFORMATION: Artificial sequence invented by inventors

<400> SEQUENCE: 3
ttgtcttatt ctttaataac at                                        22

<210> SEQ ID NO 4
<211> LENGTH: 22

-continued

```
<212> TYPE: DNA
<213> ORGANISM: Artificial Sequence
<220> FEATURE:
<223> OTHER INFORMATION: Artificial sequence invented by inventors

<400> SEQUENCE: 4
atgttattaa agaataagac aa                                              22

<210> SEQ ID NO 5
<211> LENGTH: 22
<212> TYPE: DNA
<213> ORGANISM: Artificial Sequence
<220> FEATURE:
<223> OTHER INFORMATION: Artificial sequence invented by inventors

<400> SEQUENCE: 5
ttgtcttact cttcaataac at                                              22

<210> SEQ ID NO 6
<211> LENGTH: 22
<212> TYPE: DNA
<213> ORGANISM: Artificial Sequence
<220> FEATURE:
<223> OTHER INFORMATION: Artificial sequence invented by inventors

<400> SEQUENCE: 6
accaacatgt ctcttctcct at                                              22

<210> SEQ ID NO 7
<211> LENGTH: 20
<212> TYPE: DNA
<213> ORGANISM: Artificial Sequence
<220> FEATURE:
<223> OTHER INFORMATION: Artificial sequence invented by inventors

<400> SEQUENCE: 7
tagtgataac tcatagtaca                                                 20

<210> SEQ ID NO 8
<211> LENGTH: 20
<212> TYPE: DNA
<213> ORGANISM: Artificial Sequence
<220> FEATURE:
<223> OTHER INFORMATION: Artificial sequence invented by inventors

<400> SEQUENCE: 8
tgtactatga gttatcacta                                                 20

<210> SEQ ID NO 9
<211> LENGTH: 21
<212> TYPE: DNA
<213> ORGANISM: Artificial Sequence
<220> FEATURE:
<223> OTHER INFORMATION: Artificial sequence invented by inventors

<400> SEQUENCE: 9
ccgccatgtc tgttacgtta a                                               21

<210> SEQ ID NO 10
<211> LENGTH: 21
<212> TYPE: DNA
<213> ORGANISM: Artificial Sequence
<220> FEATURE:
<223> OTHER INFORMATION: Artificial sequence invented by inventors

<400> SEQUENCE: 10
```
ttaacgtaac agacatggcg g                                                 21

<210> SEQ ID NO 11
<211> LENGTH: 22
<212> TYPE: DNA
<213> ORGANISM: Artificial Sequence
<220> FEATURE:
<223> OTHER INFORMATION: Artificial sequence invented by inventors

<400> SEQUENCE: 11
cgcagagagt gttatattgc at                                                22

<210> SEQ ID NO 12
<211> LENGTH: 22
<212> TYPE: DNA
<213> ORGANISM: Artificial Sequence
<220> FEATURE:
<223> OTHER INFORMATION: Artificial sequence invented by inventors

<400> SEQUENCE: 12
atgcaatata acactctctg cg                                                22

<210> SEQ ID NO 13
<211> LENGTH: 22
<212> TYPE: DNA
<213> ORGANISM: Artificial Sequence
<220> FEATURE:
<223> OTHER INFORMATION: Artificial sequence invented by inventors

<400> SEQUENCE: 13
aggaattaag gtagaggtta ta                                                22

<210> SEQ ID NO 14
<211> LENGTH: 22
<212> TYPE: DNA
<213> ORGANISM: Artificial Sequence
<220> FEATURE:
<223> OTHER INFORMATION: Artificial sequence invented by inventors

<400> SEQUENCE: 14
tataacctct accttaattc ct                                                22

<210> SEQ ID NO 15
<211> LENGTH: 21
<212> TYPE: DNA
<213> ORGANISM: Artificial Sequence
<220> FEATURE:
<223> OTHER INFORMATION: Artificial sequence invented by inventors

<400> SEQUENCE: 15
aggcagagaa gggtatggaa t                                                 21

<210> SEQ ID NO 16
<211> LENGTH: 21
<212> TYPE: DNA
<213> ORGANISM: Artificial Sequence
<220> FEATURE:
<223> OTHER INFORMATION: Artificial sequence invented by inventors

<400> SEQUENCE: 16
attccatacc cttctctgcc t                                                 21

<210> SEQ ID NO 17
<211> LENGTH: 19
<212> TYPE: RNA
<213> ORGANISM: Artificial Sequence

```
<220> FEATURE:
<223> OTHER INFORMATION: Example Loop Sequence for use in miR constructs
      with amiR stem sequence

<400> SEQUENCE: 17
uagugaagcc acagaugua                                                    19

<210> SEQ ID NO 18
<211> LENGTH: 28
<212> TYPE: DNA
<213> ORGANISM: Artificial Sequence
<220> FEATURE:
<223> OTHER INFORMATION: Exemplary [Z] Sequence construct

<400> SEQUENCE: 18
gaaggtatat tgctgttgac agtgagcg                                          28

<210> SEQ ID NO 19
<211> LENGTH: 15
<212> TYPE: DNA
<213> ORGANISM: Artificial Sequence
<220> FEATURE:
<223> OTHER INFORMATION: Exemplary [Z'] Sequence

<400> SEQUENCE: 19
tgcctactgc ctcgg                                                        15

<210> SEQ ID NO 20
<211> LENGTH: 24
<212> TYPE: DNA
<213> ORGANISM: Artificial Sequence
<220> FEATURE:
<223> OTHER INFORMATION: Derived from hsa-miR143

<400> SEQUENCE: 20
gcgcagcgcc cugucuccca gccu                                              24

<210> SEQ ID NO 21
<211> LENGTH: 25
<212> TYPE: DNA
<213> ORGANISM: Artificial Sequence
<220> FEATURE:
<223> OTHER INFORMATION: Derived from hsa-miR143

<400> SEQUENCE: 21
aggaagagag aaguuguucu gcagc                                             25

<210> SEQ ID NO 22
<211> LENGTH: 11
<212> TYPE: DNA
<213> ORGANISM: Artificial Sequence
<220> FEATURE:
<223> OTHER INFORMATION: Derived from hsa-miR143

<400> SEQUENCE: 22
caguugggag u                                                            11

<210> SEQ ID NO 23
<211> LENGTH: 10
<212> TYPE: DNA
<213> ORGANISM: Artificial Sequence
<220> FEATURE:
<223> OTHER INFORMATION: Derived from hsa-miR-99a

<400> SEQUENCE: 23
cccauuggca                                                              10
```

```
<210> SEQ ID NO 24
<211> LENGTH: 10
<212> TYPE: DNA
<213> ORGANISM: Artificial Sequence
<220> FEATURE:
<223> OTHER INFORMATION: Derived from hsa-miR-99a

<400> SEQUENCE: 24
ugucagugug                                                           10

<210> SEQ ID NO 25
<211> LENGTH: 15
<212> TYPE: DNA
<213> ORGANISM: Artificial Sequence
<220> FEATURE:
<223> OTHER INFORMATION: Derived from hsa-miR-99a

<400> SEQUENCE: 25
gugaagugga ccgca                                                     15

<210> SEQ ID NO 26
<211> LENGTH: 11
<212> TYPE: DNA
<213> ORGANISM: Artificial Sequence
<220> FEATURE:
<223> OTHER INFORMATION: Derived from hsa-miR-3928

<400> SEQUENCE: 26
gggcaggaag c                                                         11

<210> SEQ ID NO 27
<211> LENGTH: 12
<212> TYPE: DNA
<213> ORGANISM: Artificial Sequence
<220> FEATURE:
<223> OTHER INFORMATION: Derived from hsa-miR-150

<400> SEQUENCE: 27
cuccccaugg cc                                                        12

<210> SEQ ID NO 28
<211> LENGTH: 12
<212> TYPE: DNA
<213> ORGANISM: Artificial Sequence
<220> FEATURE:
<223> OTHER INFORMATION: [B] Sequence Derived from hsa-miR-150

<400> SEQUENCE: 28
ggaccugggg ac                                                        12

<210> SEQ ID NO 29
<211> LENGTH: 13
<212> TYPE: DNA
<213> ORGANISM: Artificial Sequence
<220> FEATURE:
<223> OTHER INFORMATION: Derived from hsa-miR-150

<400> SEQUENCE: 29
cugggcucag acc                                                       13

<210> SEQ ID NO 30
<211> LENGTH: 16
<212> TYPE: DNA
<213> ORGANISM: Artificial Sequence
<220> FEATURE:
```

```
<223> OTHER INFORMATION: Derived from hsa-miR-451a

<400> SEQUENCE: 30
cuugggaaug gcaagg                                              16

<210> SEQ ID NO 31
<211> LENGTH: 16
<212> TYPE: DNA
<213> ORGANISM: Artificial Sequence
<220> FEATURE:
<223> OTHER INFORMATION: Derived from hsa-miR451a

<400> SEQUENCE: 31
ucuugcuaua cccaga                                              16

<210> SEQ ID NO 32
<211> LENGTH: 4
<212> TYPE: DNA
<213> ORGANISM: Artificial Sequence
<220> FEATURE:
<223> OTHER INFORMATION: Derived from hsa-miR-451a

<400> SEQUENCE: 32 aguu                                                            4

<210> SEQ ID NO 33
<211> LENGTH: 23
<212> TYPE: DNA
<213> ORGANISM: Artificial Sequence
<220> FEATURE:
<223> OTHER INFORMATION: Derived from hsa-miR-331

<400> SEQUENCE: 33
gaguuugguu uuguuugggu uug                                      23

<210> SEQ ID NO 34
<211> LENGTH: 13
<212> TYPE: DNA
<213> ORGANISM: Artificial Sequence
<220> FEATURE:
<223> OTHER INFORMATION: Derived from hsa-miR-331

<400> SEQUENCE: 34
ccaaccuaag cuc                                                 13

<210> SEQ ID NO 35
<211> LENGTH: 13
<212> TYPE: DNA
<213> ORGANISM: Artificial Sequence
<220> FEATURE:
<223> OTHER INFORMATION: Derived from hsa-miR-331

<400> SEQUENCE: 35
cagaucaaac cag                                                 13

<210> SEQ ID NO 36
<211> LENGTH: 6
<212> TYPE: DNA
<213> ORGANISM: Artificial Sequence
<220> FEATURE:
<223> OTHER INFORMATION: Derived from hsa-miR-369

<400> SEQUENCE: 36 uugaag                                                          6
```

```
<210> SEQ ID NO 37
<211> LENGTH: 6
<212> TYPE: DNA
<213> ORGANISM: Artificial Sequence
<220> FEATURE:
<223> OTHER INFORMATION: Derived from hsa-miR-369

<400> SEQUENCE: 37 ucucag                                                                  6

<210> SEQ ID NO 38
<211> LENGTH: 13
<212> TYPE: DNA
<213> ORGANISM: Artificial Sequence
<220> FEATURE:
<223> OTHER INFORMATION: Derived from hsa-miR-369

<400> SEQUENCE: 38
uuuauugacu ucg                                                         13

<210> SEQ ID NO 39
<211> LENGTH: 14
<212> TYPE: DNA
<213> ORGANISM: Artificial Sequence
<220> FEATURE:
<223> OTHER INFORMATION: Derived from hsa-miR-30b

<400> SEQUENCE: 39
accaaguuuc aguu                                                        14

<210> SEQ ID NO 40
<211> LENGTH: 12
<212> TYPE: DNA
<213> ORGANISM: Artificial Sequence
<220> FEATURE:
<223> OTHER INFORMATION: Derived from hsa-miR-30b

<400> SEQUENCE: 40
agcugacuug ga                                                          12

<210> SEQ ID NO 41
<211> LENGTH: 16
<212> TYPE: DNA
<213> ORGANISM: Artificial Sequence
<220> FEATURE:
<223> OTHER INFORMATION: Derived from hsa-miR-30b

<400> SEQUENCE: 41
guaauacaug gauugg                                                      16

<210> SEQ ID NO 42
<211> LENGTH: 13
<212> TYPE: DNA
<213> ORGANISM: Artificial Sequence
<220> FEATURE:
<223> OTHER INFORMATION: Derived from hsa-miR-494

<400> SEQUENCE: 42
gauacucgaa gga                                                         13

<210> SEQ ID NO 43
<211> LENGTH: 12
<212> TYPE: DNA
<213> ORGANISM: Artificial Sequence
<220> FEATURE:
<223> OTHER INFORMATION: Derived from hsa-miR-494
```

```
<400> SEQUENCE: 43
uuuuuuagua uc                                                          12

<210> SEQ ID NO 44
<211> LENGTH: 10
<212> TYPE: DNA
<213> ORGANISM: Artificial Sequence
<220> FEATURE:
<223> OTHER INFORMATION: Derived from hsa-miR-494

<400> SEQUENCE: 44
uuauuuauga                                                             10

<210> SEQ ID NO 45
<211> LENGTH: 12
<212> TYPE: DNA
<213> ORGANISM: Artificial Sequence
<220> FEATURE:
<223> OTHER INFORMATION: Derived from hsa-miR-1305

<400> SEQUENCE: 45
aagauccugc ug                                                          12

<210> SEQ ID NO 46
<211> LENGTH: 14
<212> TYPE: DNA
<213> ORGANISM: Artificial Sequence
<220> FEATURE:
<223> OTHER INFORMATION: Derived from hsa-miR-1305

<400> SEQUENCE: 46
cagcaggauu cucc                                                        14

<210> SEQ ID NO 47
<211> LENGTH: 14
<212> TYPE: DNA
<213> ORGANISM: Artificial Sequence
<220> FEATURE:
<223> OTHER INFORMATION: Derived from hsa-miR-1305

<400> SEQUENCE: 47
uauuguaaag auac                                                        14

<210> SEQ ID NO 48
<211> LENGTH: 2
<212> TYPE: DNA
<213> ORGANISM: Artificial Sequence
<220> FEATURE:
<223> OTHER INFORMATION: Derived from hsa-miR-362

<400> SEQUENCE: 48 cu                                                                      2

<210> SEQ ID NO 49
<211> LENGTH: 2
<212> TYPE: DNA
<213> ORGANISM: Artificial Sequence
<220> FEATURE:
<223> OTHER INFORMATION: Derived from hsa-miR-362

<400> SEQUENCE: 49 aa                                                                      2

<210> SEQ ID NO 50
<211> LENGTH: 13
```

```
<212> TYPE: DNA
<213> ORGANISM: Artificial Sequence
<220> FEATURE:
<223> OTHER INFORMATION: Derived from hsa-miR-362

<400> SEQUENCE: 50
gcuauuucag ugc                                                          13

<210> SEQ ID NO 51
<211> LENGTH: 18
<212> TYPE: DNA
<213> ORGANISM: Artificial Sequence
<220> FEATURE:
<223> OTHER INFORMATION: [A] Sequence Derived from hsa-miR-219a-1

<400> SEQUENCE: 51
ccgccccggg ccgcggcu                                                     18

<210> SEQ ID NO 52
<211> LENGTH: 27
<212> TYPE: DNA
<213> ORGANISM: Artificial Sequence
<220> FEATURE:
<223> OTHER INFORMATION: Derived from hsa-miR-219a-1

<400> SEQUENCE: 52
agccgccgcc cccaaaccuc gagcggg                                           27

<210> SEQ ID NO 53
<211> LENGTH: 20
<212> TYPE: DNA
<213> ORGANISM: Artificial Sequence
<220> FEATURE:
<223> OTHER INFORMATION: Derived from hsa-miR-219a-1

<400> SEQUENCE: 53
cgagucuaug gcuccggccg                                                   20

<210> SEQ ID NO 54
<211> LENGTH: 13
<212> TYPE: DNA
<213> ORGANISM: Artificial Sequence
<220> FEATURE:
<223> OTHER INFORMATION: Derived from hsa-miR-142

<400> SEQUENCE: 54
gacagugcag uca                                                          13

<210> SEQ ID NO 55
<211> LENGTH: 13
<212> TYPE: DNA
<213> ORGANISM: Artificial Sequence
<220> FEATURE:
<223> OTHER INFORMATION: Derived from hsa-miR-142

<400> SEQUENCE: 55
ugaguguacu gug                                                          13

<210> SEQ ID NO 56
<211> LENGTH: 15
<212> TYPE: DNA
<213> ORGANISM: Artificial Sequence
<220> FEATURE:
<223> OTHER INFORMATION: Derived from hsa-miR-142

<400> SEQUENCE: 56
```

```
aacagcacug gaggg                                                    15

<210> SEQ ID NO 57
<211> LENGTH: 7
<212> TYPE: DNA
<213> ORGANISM: Artificial Sequence
<220> FEATURE:
<223> OTHER INFORMATION: Derived from hsa-miR-744

<400> SEQUENCE: 57 uugggca                                                              7

<210> SEQ ID NO 58
<211> LENGTH: 9
<212> TYPE: DNA
<213> ORGANISM: Artificial Sequence
<220> FEATURE:
<223> OTHER INFORMATION: Derived from hsa-miR-744

<400> SEQUENCE: 58 uacucgguc                                                            9

<210> SEQ ID NO 59
<211> LENGTH: 35
<212> TYPE: DNA
<213> ORGANISM: Artificial Sequence
<220> FEATURE:
<223> OTHER INFORMATION: Derived from hsa-miR-744

<400> SEQUENCE: 59
gucuuacuga agguuccug gaaccacgc acaug                                35

<210> SEQ ID NO 60
<211> LENGTH: 13
<212> TYPE: DNA
<213> ORGANISM: Artificial Sequence
<220> FEATURE:
<223> OTHER INFORMATION: Derived from hsa-miR-3619

<400> SEQUENCE: 60
acggcaucuu ugc                                                      13

<210> SEQ ID NO 61
<211> LENGTH: 15
<212> TYPE: DNA
<213> ORGANISM: Artificial Sequence
<220> FEATURE:
<223> OTHER INFORMATION: Derived from hsa-miR-3619

<400> SEQUENCE: 61
gguaaggacg gcugu                                                    15

<210> SEQ ID NO 62
<211> LENGTH: 9
<212> TYPE: DNA
<213> ORGANISM: Artificial Sequence
<220> FEATURE:
<223> OTHER INFORMATION: Derived from hsa-miR-3619

<400> SEQUENCE: 62 ccguggugg                                                            9

<210> SEQ ID NO 63
<211> LENGTH: 10
<212> TYPE: DNA
<213> ORGANISM: Artificial Sequence
```

```
<220> FEATURE:
<223> OTHER INFORMATION: Derived from hsa-miR-4725

<400> SEQUENCE: 63
gugucucucu                                                              10

<210> SEQ ID NO 64
<211> LENGTH: 11
<212> TYPE: DNA
<213> ORGANISM: Artificial Sequence
<220> FEATURE:
<223> OTHER INFORMATION: Derived from hsa-miR-4725

<400> SEQUENCE: 64
ugagggaaca c                                                            11

<210> SEQ ID NO 65
<211> LENGTH: 24
<212> TYPE: DNA
<213> ORGANISM: Artificial Sequence
<220> FEATURE:
<223> OTHER INFORMATION: Derived from hsa-miR-4725

<400> SEQUENCE: 65
caccagggag cuuccaugg gcug                                               24

<210> SEQ ID NO 66
<211> LENGTH: 5
<212> TYPE: DNA
<213> ORGANISM: Artificial Sequence
<220> FEATURE:
<223> OTHER INFORMATION: Derived from hsa-miR-6886

<400> SEQUENCE: 66 cuugg                                                                    5

<210> SEQ ID NO 67
<211> LENGTH: 2
<212> TYPE: DNA
<213> ORGANISM: Artificial Sequence
<220> FEATURE:
<223> OTHER INFORMATION: Derived from hsa-miR-6886

<400> SEQUENCE: 67 ag                                                                       2

<210> SEQ ID NO 68
<211> LENGTH: 11
<212> TYPE: DNA
<213> ORGANISM: Artificial Sequence
<220> FEATURE:
<223> OTHER INFORMATION: Derived from hsa-miR-6886

<400> SEQUENCE: 68
ccuggcgcug a                                                            11

<210> SEQ ID NO 69
<211> LENGTH: 15
<212> TYPE: DNA
<213> ORGANISM: Artificial Sequence
<220> FEATURE:
<223> OTHER INFORMATION: Derived from hsa-miR-615

<400> SEQUENCE: 69
cucgggaggg gcggg                                                        15
```

```
<210> SEQ ID NO 70
<211> LENGTH: 14
<212> TYPE: DNA
<213> ORGANISM: Artificial Sequence
<220> FEATURE:
<223> OTHER INFORMATION: Derived from hsa-miR-615

<400> SEQUENCE: 70
ccccccaacc cccc                                                         14

<210> SEQ ID NO 71
<211> LENGTH: 21
<212> TYPE: DNA
<213> ORGANISM: Artificial Sequence
<220> FEATURE:
<223> OTHER INFORMATION: Derived from hsa-miR-615

<400> SEQUENCE: 71
ucgagggugc uuauuguucg g                                                 21

<210> SEQ ID NO 72
<211> LENGTH: 13
<212> TYPE: DNA
<213> ORGANISM: Artificial Sequence
<220> FEATURE:
<223> OTHER INFORMATION: Derived from hsa-miR-2116

<400> SEQUENCE: 72
gaccuaggcu agg                                                          13

<210> SEQ ID NO 73
<211> LENGTH: 9
<212> TYPE: DNA
<213> ORGANISM: Artificial Sequence
<220> FEATURE:
<223> OTHER INFORMATION: [B] Sequence Derived from hsa-miR-2116

<400> SEQUENCE: 73 agacuagga                                                                9

<210> SEQ ID NO 74
<211> LENGTH: 16
<212> TYPE: DNA
<213> ORGANISM: Artificial Sequence
<220> FEATURE:
<223> OTHER INFORMATION: Derived from hsa-miR-2116

<400> SEQUENCE: 74
ucccaugcua agaagu                                                       16

<210> SEQ ID NO 75
<211> LENGTH: 9
<212> TYPE: DNA
<213> ORGANISM: Artificial Sequence
<220> FEATURE:
<223> OTHER INFORMATION: Derived from hsa-miR-3157

<400> SEQUENCE: 75 gggaagggc                                                                9

<210> SEQ ID NO 76
<211> LENGTH: 6
<212> TYPE: DNA
<213> ORGANISM: Artificial Sequence
<220> FEATURE:
<223> OTHER INFORMATION: Derived from hsa-miR-3157
```

```
<400> SEQUENCE: 76 uuuccc                                                                        6

<210> SEQ ID NO 77
<211> LENGTH: 26
<212> TYPE: DNA
<213> ORGANISM: Artificial Sequence
<220> FEATURE:
<223> OTHER INFORMATION: Derived from hsa-miR-3157

<400> SEQUENCE: 77
gcuuugugcc aacacugggg ugauga                                                 26

<210> SEQ ID NO 78
<211> LENGTH: 13
<212> TYPE: DNA
<213> ORGANISM: Artificial Sequence
<220> FEATURE:
<223> OTHER INFORMATION: Derived from hsa-miR-642a

<400> SEQUENCE: 78
aucugaguug gga                                                               13

<210> SEQ ID NO 79
<211> LENGTH: 25
<212> TYPE: DNA
<213> ORGANISM: Artificial Sequence
<220> FEATURE:
<223> OTHER INFORMATION: Derived from hsa-miR-642a

<400> SEQUENCE: 79
ucccaacucg gccucugcca ucauu                                                  25

<210> SEQ ID NO 80
<211> LENGTH: 13
<212> TYPE: DNA
<213> ORGANISM: Artificial Sequence
<220> FEATURE:
<223> OTHER INFORMATION: Derived from hsa-miR-642a

<400> SEQUENCE: 80 gggugggga uca                                                                13

<210> SEQ ID NO 81
<211> LENGTH: 26
<212> TYPE: DNA
<213> ORGANISM: Artificial Sequence
<220> FEATURE:
<223> OTHER INFORMATION: Derived from hsa-miR-766

<400> SEQUENCE: 81
gcauccucag gaccugggcu ugggug                                                 26

<210> SEQ ID NO 82
<211> LENGTH: 25
<212> TYPE: DNA
<213> ORGANISM: Artificial Sequence
<220> FEATURE:
<223> OTHER INFORMATION: Derived from hsa-miR-766

<400> SEQUENCE: 82
caccccagcc aaugucaua ggagc                                                   25

<210> SEQ ID NO 83
```

-continued

<210> SEQ ID NO 83 (implied)
<211> LENGTH: 14
<212> TYPE: DNA
<213> ORGANISM: Artificial Sequence
<220> FEATURE:
<223> OTHER INFORMATION: Derived from hsa-miR-766

<400> SEQUENCE: 83
ucauuuugga uuug                                                        14

<210> SEQ ID NO 84
<211> LENGTH: 7
<212> TYPE: DNA
<213> ORGANISM: Artificial Sequence
<220> FEATURE:
<223> OTHER INFORMATION: Derived from hsa-miR-484

<400> SEQUENCE: 84 agccucg                                                                 7

<210> SEQ ID NO 85
<211> LENGTH: 11
<212> TYPE: DNA
<213> ORGANISM: Artificial Sequence
<220> FEATURE:
<223> OTHER INFORMATION: Derived from hsa-miR-484

<400> SEQUENCE: 85 cuuuuuggc g                                                            11

<210> SEQ ID NO 86
<211> LENGTH: 21
<212> TYPE: DNA
<213> ORGANISM: Artificial Sequence
<220> FEATURE:
<223> OTHER INFORMATION: Derived from hsa-miR-484

<400> SEQUENCE: 86 aaacccuaa auagggacuu u                                                 21

<210> SEQ ID NO 87
<211> LENGTH: 24
<212> TYPE: DNA
<213> ORGANISM: Artificial Sequence
<220> FEATURE:
<223> OTHER INFORMATION: Derived from hsa-miR-181c

<400> SEQUENCE: 87
cggaaaauuu gccaaggguu uggg                                             24

<210> SEQ ID NO 88
<211> LENGTH: 24
<212> TYPE: DNA
<213> ORGANISM: Artificial Sequence
<220> FEATURE:
<223> OTHER INFORMATION: Derived from hsa-miR181c

<400> SEQUENCE: 88
ccugaggccu ggaauugcca uccu                                             24

<210> SEQ ID NO 89
<211> LENGTH: 16
<212> TYPE: DNA
<213> ORGANISM: Artificial Sequence
<220> FEATURE:
<223> OTHER INFORMATION: Derived from hsa-miR-181c

<400> SEQUENCE: 89

```
uugggcagcu caggca                                             16

<210> SEQ ID NO 90
<211> LENGTH: 25
<212> TYPE: DNA
<213> ORGANISM: Artificial Sequence
<220> FEATURE:
<223> OTHER INFORMATION: Derived from hsa-miR-10b

<400> SEQUENCE: 90
ccagagguug uaacguuguc uauau                                   25

<210> SEQ ID NO 91
<211> LENGTH: 23
<212> TYPE: DNA
<213> ORGANISM: Artificial Sequence
<220> FEATURE:
<223> OTHER INFORMATION: Derived from hsa-miR-10b

<400> SEQUENCE: 91
auauggucga ugcaaaaacu uca                                     23

<210> SEQ ID NO 92
<211> LENGTH: 16
<212> TYPE: DNA
<213> ORGANISM: Artificial Sequence
<220> FEATURE:
<223> OTHER INFORMATION: Derived from hsa-miR-10b

<400> SEQUENCE: 92
ugguauccgu auaguc                                             16

<210> SEQ ID NO 93
<211> LENGTH: 3
<212> TYPE: DNA
<213> ORGANISM: Artificial Sequence
<220> FEATURE:
<223> OTHER INFORMATION: Derived from hsa-miR-199a1

<400> SEQUENCE: 93 gcc                                                            3

<210> SEQ ID NO 94
<211> LENGTH: 3
<212> TYPE: DNA
<213> ORGANISM: Artificial Sequence
<220> FEATURE:
<223> OTHER INFORMATION: Derived from hsa-miR-199a1

<400> SEQUENCE: 94 ggc                                                            3

<210> SEQ ID NO 95
<211> LENGTH: 18
<212> TYPE: DNA
<213> ORGANISM: Artificial Sequence
<220> FEATURE:
<223> OTHER INFORMATION: Derived from hsa-miR-199a1

<400> SEQUENCE: 95
aggaggcucu caaugugu                                           18

<210> SEQ ID NO 96
<211> LENGTH: 19
<212> TYPE: DNA
```

```
<213> ORGANISM: Artificial Sequence
<220> FEATURE:
<223> OTHER INFORMATION: Derived from hsa-miR-659

<400> SEQUENCE: 96
uaccgacccu cgauuuggu                                                    19

<210> SEQ ID NO 97
<211> LENGTH: 15
<212> TYPE: DNA
<213> ORGANISM: Artificial Sequence
<220> FEATURE:
<223> OTHER INFORMATION: Derived from hsa-miR-659

<400> SEQUENCE: 97
acaauguccu caugg                                                        15

<210> SEQ ID NO 98
<211> LENGTH: 17
<212> TYPE: DNA
<213> ORGANISM: Artificial Sequence
<220> FEATURE:
<223> OTHER INFORMATION: Derived from hsa-miR-659

<400> SEQUENCE: 98
agagucacag ucucuuc                                                      17

<210> SEQ ID NO 99
<211> LENGTH: 3
<212> TYPE: DNA
<213> ORGANISM: Artificial Sequence
<220> FEATURE:
<223> OTHER INFORMATION: Derived from hsa-miR-6511a

<400> SEQUENCE: 99 ccu                                                                      3

<210> SEQ ID NO 100
<211> LENGTH: 2
<212> TYPE: DNA
<213> ORGANISM: Artificial Sequence
<220> FEATURE:
<223> OTHER INFORMATION: Derived from hsa-miR-6511a

<400> SEQUENCE: 100 ag                                                                       2

<210> SEQ ID NO 101
<211> LENGTH: 16
<212> TYPE: DNA
<213> ORGANISM: Artificial Sequence
<220> FEATURE:
<223> OTHER INFORMATION: Derived from hsa-miR-6511a

<400> SEQUENCE: 101
gcagaggguu gcgccc                                                       16

<210> SEQ ID NO 102
<211> LENGTH: 5
<212> TYPE: DNA
<213> ORGANISM: Artificial Sequence
<220> FEATURE:
<223> OTHER INFORMATION: Derived from hsa-miR-381

<400> SEQUENCE: 102 uacuu                                                                    5
```

<210> SEQ ID NO 103
<211> LENGTH: 5
<212> TYPE: DNA
<213> ORGANISM: Artificial Sequence
<220> FEATURE:
<223> OTHER INFORMATION: Derived from hsa-miR-381

<400> SEQUENCE: 103 gagua                                                                 5

<210> SEQ ID NO 104
<211> LENGTH: 19
<212> TYPE: DNA
<213> ORGANISM: Artificial Sequence
<220> FEATURE:
<223> OTHER INFORMATION: Derived from hsa-miR-381

<400> SEQUENCE: 104
ucgguuuauu gacauggaa                                                 19

<210> SEQ ID NO 105
<211> LENGTH: 12
<212> TYPE: DNA
<213> ORGANISM: Artificial Sequence
<220> FEATURE:
<223> OTHER INFORMATION: Derived from hsa-miR-122

<400> SEQUENCE: 105
ccuuagcaga gc                                                        12

<210> SEQ ID NO 106
<211> LENGTH: 13
<212> TYPE: DNA
<213> ORGANISM: Artificial Sequence
<220> FEATURE:
<223> OTHER INFORMATION: Derived from hsa-miR-122

<400> SEQUENCE: 106
gcuacugcua ggc                                                       13

<210> SEQ ID NO 107
<211> LENGTH: 14
<212> TYPE: DNA
<213> ORGANISM: Artificial Sequence
<220> FEATURE:
<223> OTHER INFORMATION: Derived from hsa-miR-122

<400> SEQUENCE: 107
ugucuaaacu auca                                                      14

<210> SEQ ID NO 108
<211> LENGTH: 15
<212> TYPE: DNA
<213> ORGANISM: Artificial Sequence
<220> FEATURE:
<223> OTHER INFORMATION: Derived from hsa-miR-449a

<400> SEQUENCE: 108
cuguguguga ugagc                                                     15

<210> SEQ ID NO 109
<211> LENGTH: 16
<212> TYPE: DNA
<213> ORGANISM: Artificial Sequence
<220> FEATURE:

```
<223> OTHER INFORMATION: Derived from hsa-miR-449a

<400> SEQUENCE: 109
ucuuauugca uauaca                                                      16

<210> SEQ ID NO 110
<211> LENGTH: 16
<212> TYPE: DNA
<213> ORGANISM: Artificial Sequence
<220> FEATURE:
<223> OTHER INFORMATION: Derived from hsa-miR-449a

<400> SEQUENCE: 110
ugaauaugug aauggc                                                      16

<210> SEQ ID NO 111
<211> LENGTH: 13
<212> TYPE: DNA
<213> ORGANISM: Artificial Sequence
<220> FEATURE:
<223> OTHER INFORMATION: Derived from hsa-miR-152

<400> SEQUENCE: 111
uguccccccc ggc                                                         13

<210> SEQ ID NO 112
<211> LENGTH: 13
<212> TYPE: DNA
<213> ORGANISM: Artificial Sequence
<220> FEATURE:
<223> OTHER INFORMATION: Derived from hsa-miR-152

<400> SEQUENCE: 112
gcccggaagg acc                                                         13

<210> SEQ ID NO 113
<211> LENGTH: 15
<212> TYPE: DNA
<213> ORGANISM: Artificial Sequence
<220> FEATURE:
<223> OTHER INFORMATION: Derived from hsa-miR-152

<400> SEQUENCE: 113
cgggcucugg agcag                                                       15

<210> SEQ ID NO 114
<211> LENGTH: 8
<212> TYPE: DNA
<213> ORGANISM: Artificial Sequence
<220> FEATURE:
<223> OTHER INFORMATION: Derived from hsa-miR-3129

<400> SEQUENCE: 114 guacuugg                                                                8

<210> SEQ ID NO 115
<211> LENGTH: 8
<212> TYPE: DNA
<213> ORGANISM: Artificial Sequence
<220> FEATURE:
<223> OTHER INFORMATION: Derived from hsa-miR-3219

<400> SEQUENCE: 115 ccaagagc                                                                8
```

```
<210> SEQ ID NO 116
<211> LENGTH: 16
<212> TYPE: DNA
<213> ORGANISM: Artificial Sequence
<220> FEATURE:
<223> OTHER INFORMATION: Derived from hsa-miR-3129

<400> SEQUENCE: 116
gccuguuaau gaauuc                                                      16

<210> SEQ ID NO 117
<211> LENGTH: 6
<212> TYPE: DNA
<213> ORGANISM: Artificial Sequence
<220> FEATURE:
<223> OTHER INFORMATION: Derived from hsa-miR-31

<400> SEQUENCE: 117 ggagag                                                                  6

<210> SEQ ID NO 118
<211> LENGTH: 6
<212> TYPE: DNA
<213> ORGANISM: Artificial Sequence
<220> FEATURE:
<223> OTHER INFORMATION: Derived from hsa-miR-31

<400> SEQUENCE: 118 cuuucc                                                                  6

<210> SEQ ID NO 119
<211> LENGTH: 15
<212> TYPE: DNA
<213> ORGANISM: Artificial Sequence
<220> FEATURE:
<223> OTHER INFORMATION: Derived from hsa-miR-31

<400> SEQUENCE: 119
guugaacugg gaacc                                                       15

<210> SEQ ID NO 120
<211> LENGTH: 11
<212> TYPE: DNA
<213> ORGANISM: Artificial Sequence
<220> FEATURE:
<223> OTHER INFORMATION: Derived from hsa-miR-95

<400> SEQUENCE: 120
aacacagugg g                                                           11

<210> SEQ ID NO 121
<211> LENGTH: 11
<212> TYPE: DNA
<213> ORGANISM: Artificial Sequence
<220> FEATURE:
<223> OTHER INFORMATION: Derived from hsa-miR-95

<400> SEQUENCE: 121
cccacucugu g                                                           11

<210> SEQ ID NO 122
<211> LENGTH: 13
<212> TYPE: DNA
<213> ORGANISM: Artificial Sequence
<220> FEATURE:
<223> OTHER INFORMATION: Derived from hsa-miR-95
```

<400> SEQUENCE: 122
gaaaugcguu aca                                                    13

<210> SEQ ID NO 123
<211> LENGTH: 30
<212> TYPE: DNA
<213> ORGANISM: Artificial Sequence
<220> FEATURE:
<223> OTHER INFORMATION: Derived from hsa-miR-204

<400> SEQUENCE: 123
ggcuacaguc uuucuucaug ugacucgugg                                  30

<210> SEQ ID NO 124
<211> LENGTH: 18
<212> TYPE: DNA
<213> ORGANISM: Artificial Sequence
<220> FEATURE:
<223> OTHER INFORMATION: Derived from hsa-miR-204

<400> SEQUENCE: 124
ucaauuguca ucacuggc                                               18

<210> SEQ ID NO 125
<211> LENGTH: 17
<212> TYPE: DNA
<213> ORGANISM: Artificial Sequence
<220> FEATURE:
<223> OTHER INFORMATION: Derived from hsa-miR-204

<400> SEQUENCE: 125
gagaauauau gaaggag                                                17

<210> SEQ ID NO 126
<211> LENGTH: 15
<212> TYPE: DNA
<213> ORGANISM: Artificial Sequence
<220> FEATURE:
<223> OTHER INFORMATION: Derived from hsa-miR-577

<400> SEQUENCE: 126 uggggagug aagag                                                   15

<210> SEQ ID NO 127
<211> LENGTH: 26
<212> TYPE: DNA
<213> ORGANISM: Artificial Sequence
<220> FEATURE:
<223> OTHER INFORMATION: Derived from hsa-miR-577

<400> SEQUENCE: 127
cucuucauuu ccccauaucu acuuac                                      26

<210> SEQ ID NO 128
<211> LENGTH: 13
<212> TYPE: DNA
<213> ORGANISM: Artificial Sequence
<220> FEATURE:
<223> OTHER INFORMATION: Derived from hsa-miR-577

<400> SEQUENCE: 128
augaaucuga ggc                                                    13

<210> SEQ ID NO 129
<211> LENGTH: 11

```
<212> TYPE: DNA
<213> ORGANISM: Artificial Sequence
<220> FEATURE:
<223> OTHER INFORMATION: Derived from hsa-miR-518b

<400> SEQUENCE: 129
ucaugcugug g                                                             11

<210> SEQ ID NO 130
<211> LENGTH: 11
<212> TYPE: DNA
<213> ORGANISM: Artificial Sequence
<220> FEATURE:
<223> OTHER INFORMATION: Derived from hsa-miR-518b

<400> SEQUENCE: 130
uuacgguuug a                                                             11

<210> SEQ ID NO 131
<211> LENGTH: 15
<212> TYPE: DNA
<213> ORGANISM: Artificial Sequence
<220> FEATURE:
<223> OTHER INFORMATION: Derived from hsa-miR-518b

<400> SEQUENCE: 131
uugucugaaa gaaaa                                                         15

<210> SEQ ID NO 132
<211> LENGTH: 6
<212> TYPE: DNA
<213> ORGANISM: Artificial Sequence
<220> FEATURE:
<223> OTHER INFORMATION: Derived from hsv1-miR-H5-3p

<400> SEQUENCE: 132 gcgcuc                                                                    6

<210> SEQ ID NO 133
<211> LENGTH: 6
<212> TYPE: DNA
<213> ORGANISM: Artificial Sequence
<220> FEATURE:
<223> OTHER INFORMATION: Derived from hsv1-miR-H5-3p

<400> SEQUENCE: 133 gggcgc                                                                    6

<210> SEQ ID NO 134
<211> LENGTH: 20
<212> TYPE: DNA
<213> ORGANISM: Artificial Sequence
<220> FEATURE:
<223> OTHER INFORMATION: Derived from hsv1-miR-H5-3p

<400> SEQUENCE: 134
cucagugccg ccaaucucag                                                    20

<210> SEQ ID NO 135
<211> LENGTH: 14
<212> TYPE: DNA
<213> ORGANISM: Artificial Sequence
<220> FEATURE:
<223> OTHER INFORMATION: Derived from hsv1-miR-H17-3p

<400> SEQUENCE: 135
```

```
ggcccacucg cacg                                                        14

<210> SEQ ID NO 136
<211> LENGTH: 12
<212> TYPE: DNA
<213> ORGANISM: Artificial Sequence
<220> FEATURE:
<223> OTHER INFORMATION: Derived from hsv1-miR-H17-3p

<400> SEQUENCE: 136
ugcgcgccgg cc                                                          12

<210> SEQ ID NO 137
<211> LENGTH: 27
<212> TYPE: DNA
<213> ORGANISM: Artificial Sequence
<220> FEATURE:
<223> OTHER INFORMATION: Derived from hsv1-miR-H17-3p

<400> SEQUENCE: 137
ugggcgcgcc gcugcggccc guguacg                                          27

<210> SEQ ID NO 138
<211> LENGTH: 22
<212> TYPE: DNA
<213> ORGANISM: Artificial Sequence
<220> FEATURE:
<223> OTHER INFORMATION: Derived from hsv1-miR-H16-5p

<400> SEQUENCE: 138
gcgcagagag ccucguuaag ag                                               22

<210> SEQ ID NO 139
<211> LENGTH: 22
<212> TYPE: DNA
<213> ORGANISM: Artificial Sequence
<220> FEATURE:
<223> OTHER INFORMATION: Derived from hsv1-miR-H16-5p

<400> SEQUENCE: 139
cugcugccgg gggacucuuc gc                                               22

<210> SEQ ID NO 140
<211> LENGTH: 9
<212> TYPE: DNA
<213> ORGANISM: Artificial Sequence
<220> FEATURE:
<223> OTHER INFORMATION: Derived from hsv1-miR-H16-5p

<400> SEQUENCE: 140 cacauacgc                                                               9

<210> SEQ ID NO 141
<211> LENGTH: 11
<212> TYPE: DNA
<213> ORGANISM: Artificial Sequence
<220> FEATURE:
<223> OTHER INFORMATION: Derived from hsv1-miR-H6-5p

<400> SEQUENCE: 141 cgggggggccg g                                                          11

<210> SEQ ID NO 142
<211> LENGTH: 12
<212> TYPE: DNA
<213> ORGANISM: Artificial Sequence
```

<220> FEATURE:
<223> OTHER INFORMATION: Derived from hsv1-miR-H6-5p

<400> SEQUENCE: 142
ccguuccccu cg                                                         12

<210> SEQ ID NO 143
<211> LENGTH: 19
<212> TYPE: DNA
<213> ORGANISM: Artificial Sequence
<220> FEATURE:
<223> OTHER INFORMATION: Derived from hsv1-miR-H6-5p

<400> SEQUENCE: 143
ggauggguau caggacuuc                                                  19

<210> SEQ ID NO 144
<211> LENGTH: 12
<212> TYPE: DNA
<213> ORGANISM: Artificial Sequence
<220> FEATURE:
<223> OTHER INFORMATION: Derived from hsv1-miR-H1-3p

<400> SEQUENCE: 144
cgaggggaac gg                                                         12

<210> SEQ ID NO 145
<211> LENGTH: 11
<212> TYPE: DNA
<213> ORGANISM: Artificial Sequence
<220> FEATURE:
<223> OTHER INFORMATION: Derived from hsv1-miR-H1-3p

<400> SEQUENCE: 145 ccggccccccc g                                                         11

<210> SEQ ID NO 146
<211> LENGTH: 17
<212> TYPE: DNA
<213> ORGANISM: Artificial Sequence
<220> FEATURE:
<223> OTHER INFORMATION: Derived from hsv1-miR-H1-3p

<400> SEQUENCE: 146
aguccugaua cccaucc                                                    17

<210> SEQ ID NO 147
<211> LENGTH: 17
<212> TYPE: DNA
<213> ORGANISM: Artificial Sequence
<220> FEATURE:
<223> OTHER INFORMATION: Derived from hsv1-miR-H12

<400> SEQUENCE: 147
ggagucgggc acggcgc                                                    17

<210> SEQ ID NO 148
<211> LENGTH: 14
<212> TYPE: DNA
<213> ORGANISM: Artificial Sequence
<220> FEATURE:
<223> OTHER INFORMATION: Derived from hsv1-miR-H12

<400> SEQUENCE: 148
cgcguucuca cuuc                                                       14

```
<210> SEQ ID NO 149
<211> LENGTH: 13
<212> TYPE: DNA
<213> ORGANISM: Artificial Sequence
<220> FEATURE:
<223> OTHER INFORMATION: Derived from hsv1-miR-H12

<400> SEQUENCE: 149
uaauauauau aua                                                          13

<210> SEQ ID NO 150
<211> LENGTH: 10
<212> TYPE: DNA
<213> ORGANISM: Artificial Sequence
<220> FEATURE:
<223> OTHER INFORMATION: Derived from hsv1-miR-H7-3p

<400> SEQUENCE: 150
gaagaggggg                                                              10

<210> SEQ ID NO 151
<211> LENGTH: 12
<212> TYPE: DNA
<213> ORGANISM: Artificial Sequence
<220> FEATURE:
<223> OTHER INFORMATION: Derived from hsv1-miR-H7-3p

<400> SEQUENCE: 151
uucccucuuc uc                                                           12

<210> SEQ ID NO 152
<211> LENGTH: 16
<212> TYPE: DNA
<213> ORGANISM: Artificial Sequence
<220> FEATURE:
<223> OTHER INFORMATION: Derived from hsv1-miR-H7-3p

<400> SEQUENCE: 152
uggucugggu ccgucc                                                       16

<210> SEQ ID NO 153
<211> LENGTH: 3
<212> TYPE: DNA
<213> ORGANISM: Artificial Sequence
<220> FEATURE:
<223> OTHER INFORMATION: Derived from hsv1-miR-H13

<400> SEQUENCE: 153 gcg                                                                      3

<210> SEQ ID NO 154
<211> LENGTH: 3
<212> TYPE: DNA
<213> ORGANISM: Artificial Sequence
<220> FEATURE:
<223> OTHER INFORMATION: Derived from hsv1-miR-H13

<400> SEQUENCE: 154 cgc                                                                      3

<210> SEQ ID NO 155
<211> LENGTH: 13
<212> TYPE: DNA
<213> ORGANISM: Artificial Sequence
<220> FEATURE:
<223> OTHER INFORMATION: Derived from hsv1-miR-H13
```

<400> SEQUENCE: 155
uauauauaua uua                                                              13

<210> SEQ ID NO 156
<211> LENGTH: 18
<212> TYPE: DNA
<213> ORGANISM: Artificial Sequence
<220> FEATURE:
<223> OTHER INFORMATION: shRNA targetting BRCA1 (human and mouse)

<400> SEQUENCE: 156
cacaaagtgt gaccacat                                                         18

<210> SEQ ID NO 157
<211> LENGTH: 4
<212> TYPE: DNA
<213> ORGANISM: Artificial Sequence
<220> FEATURE:
<223> OTHER INFORMATION: Prepared for hsa-miR451-based cassette

<400> SEQUENCE: 157 attt                                                                         4

<210> SEQ ID NO 158
<211> LENGTH: 18
<212> TYPE: DNA
<213> ORGANISM: Artificial Sequence
<220> FEATURE:
<223> OTHER INFORMATION: shRNA targetting BRCA1 (human and mouse)

<400> SEQUENCE: 158
atgtggtcac actttgtg                                                         18

<210> SEQ ID NO 159
<211> LENGTH: 19
<212> TYPE: DNA
<213> ORGANISM: Artificial Sequence
<220> FEATURE:
<223> OTHER INFORMATION: shRNA targetting BRCA2 (human and mouse)

<400> SEQUENCE: 159
tatcaggata tgcgaatta                                                        19

<210> SEQ ID NO 160
<211> LENGTH: 4
<212> TYPE: DNA
<213> ORGANISM: Artificial Sequence
<220> FEATURE:
<223> OTHER INFORMATION: Prepared for hsa-miR451-based cassette

<400> SEQUENCE: 160 agaa                                                                         4

<210> SEQ ID NO 161
<211> LENGTH: 18
<212> TYPE: DNA
<213> ORGANISM: Artificial Sequence
<220> FEATURE:
<223> OTHER INFORMATION: shRNA targetting BRCA2 (human and mouse)

<400> SEQUENCE: 161
taattcgcat atcctgta                                                         18

<210> SEQ ID NO 162

<210> SEQ ID NO 162
<211> LENGTH: 22
<212> TYPE: DNA
<213> ORGANISM: Artificial Sequence
<220> FEATURE:
<223> OTHER INFORMATION: shRNA targetting BRCA2 (human)

<400> SEQUENCE: 162
aactagtagg atattgttct tc                                          22

<210> SEQ ID NO 163
<211> LENGTH: 19
<212> TYPE: DNA
<213> ORGANISM: Artificial Sequence
<220> FEATURE:
<223> OTHER INFORMATION: Prepared for hsa-miR30-based cassette

<400> SEQUENCE: 163
ctgtgaagcc acagatggg                                              19

<210> SEQ ID NO 164
<211> LENGTH: 22
<212> TYPE: DNA
<213> ORGANISM: Artificial Sequence
<220> FEATURE:
<223> OTHER INFORMATION: shRNA targetting BRCA2 (human)

<400> SEQUENCE: 164
gaagaacaat atcctactag tt                                          22

<210> SEQ ID NO 165
<211> LENGTH: 18
<212> TYPE: DNA
<213> ORGANISM: Artificial Sequence
<220> FEATURE:
<223> OTHER INFORMATION: shRNA targetting mouse PDL1

<400> SEQUENCE: 165
ttcaacactg cttacgtc                                               18

<210> SEQ ID NO 166
<211> LENGTH: 4
<212> TYPE: DNA
<213> ORGANISM: Artificial Sequence
<220> FEATURE:
<223> OTHER INFORMATION: Prepared for hsa-miR451-based cassette

<400> SEQUENCE: 166 tcct                                                               4

<210> SEQ ID NO 167
<211> LENGTH: 18
<212> TYPE: DNA
<213> ORGANISM: Artificial Sequence
<220> FEATURE:
<223> OTHER INFORMATION: shRNA targetting mouse PDL1

<400> SEQUENCE: 167
gacgtaagca gtgttgaa                                               18

<210> SEQ ID NO 168
<211> LENGTH: 18
<212> TYPE: DNA
<213> ORGANISM: Artificial Sequence
<220> FEATURE:
<223> OTHER INFORMATION: shRNA targetting Luciferase

<400> SEQUENCE: 168

```
ctgggcgtta atcaaaga                                                         18

<210> SEQ ID NO 169
<211> LENGTH: 18
<212> TYPE: DNA
<213> ORGANISM: Artificial Sequence
<220> FEATURE:
<223> OTHER INFORMATION: shRNA targetting Luciferase

<400> SEQUENCE: 169
tctttgatta acgcccag                                                         18

<210> SEQ ID NO 170
<211> LENGTH: 18
<212> TYPE: DNA
<213> ORGANISM: Artificial Sequence
<220> FEATURE:
<223> OTHER INFORMATION: shRNA targetting eGFP

<400> SEQUENCE: 170
tctatatcat ggccgaca                                                         18

<210> SEQ ID NO 171
<211> LENGTH: 18
<212> TYPE: DNA
<213> ORGANISM: Artificial Sequence
<220> FEATURE:
<223> OTHER INFORMATION: shRNA targetting eGFP

<400> SEQUENCE: 171
tgtcggccat gatataga                                                         18

<210> SEQ ID NO 172
<211> LENGTH: 18
<212> TYPE: DNA
<213> ORGANISM: Artificial Sequence
<220> FEATURE:
<223> OTHER INFORMATION: shRNA targetting LacZ

<400> SEQUENCE: 172
tgacctatcc cattacgg                                                         18

<210> SEQ ID NO 173
<211> LENGTH: 18
<212> TYPE: DNA
<213> ORGANISM: Artificial Sequence
<220> FEATURE:
<223> OTHER INFORMATION: shRNA targetting LacZ

<400> SEQUENCE: 173
ccgtaatggg ataggtca                                                         18

<210> SEQ ID NO 174
<211> LENGTH: 19
<212> TYPE: DNA
<213> ORGANISM: Artificial Sequence
<220> FEATURE:
<223> OTHER INFORMATION: shRNA targetting Luciferase

<400> SEQUENCE: 174
gttggcacca gcagcgcac                                                        19

<210> SEQ ID NO 175
<211> LENGTH: 19
<212> TYPE: DNA
```

```
<213> ORGANISM: Artificial Sequence
<220> FEATURE:
<223> OTHER INFORMATION: shRNA targetting Luciferase

<400> SEQUENCE: 175
gtgcgctgct ggtgccaac                                               19

<210> SEQ ID NO 176
<211> LENGTH: 23
<212> TYPE: DNA
<213> ORGANISM: Artificial Sequence
<220> FEATURE:
<223> OTHER INFORMATION: Sense sequence derived from hsa-miR-1289-1 miR
      hairpin

<400> SEQUENCE: 176
uaaaugcaga cucuugguuu cca                                          23

<210> SEQ ID NO 177
<211> LENGTH: 23
<212> TYPE: DNA
<213> ORGANISM: Artificial Sequence
<220> FEATURE:
<223> OTHER INFORMATION: Anti-sense sequence derived from hsa-miR-1289-1
      miR hairpin

<400> SEQUENCE: 177
uggaguccag gaaucugcau uuu                                          23

<210> SEQ ID NO 178
<211> LENGTH: 106
<212> TYPE: DNA
<213> ORGANISM: Artificial Sequence
<220> FEATURE:
<223> OTHER INFORMATION: Construct based on miR30-based cassette with
      amiR1 active stem

<400> SEQUENCE: 178
gaaggtatat tgctgttgac agtgagcgat aggagaagag acatgttggt tagtgaagcc    60
acagatgtaa taggagaaga gacatgttgg ttgcctactg cctcgg                 106

<210> SEQ ID NO 179
<211> LENGTH: 106
<212> TYPE: DNA
<213> ORGANISM: Artificial Sequence
<220> FEATURE:
<223> OTHER INFORMATION: Construct based on miR30-based cassette with
      amiR2 active stem

<400> SEQUENCE: 179
gaaggtatat tgctgttgac agtgagcgtt gtcttattct ttaataacat tagtgaagcc    60
acagatgtaa tgttattaaa gaataagaca atgcctactg cctcgg                 106

<210> SEQ ID NO 180
<211> LENGTH: 106
<212> TYPE: DNA
<213> ORGANISM: Artificial Sequence
<220> FEATURE:
<223> OTHER INFORMATION: Construct based on miR30-based cassette with
      amiR3 active stem

<400> SEQUENCE: 180
gaaggtatat tgctgttgac agtgagcgtt gtcttactct tcaataacat tagtgaagcc    60
acagatgtaa ccaacatgtc tcttctccta ttgcctactg cctcgg                 106
```

<210> SEQ ID NO 181
<211> LENGTH: 102
<212> TYPE: DNA
<213> ORGANISM: Artificial Sequence
<220> FEATURE:
<223> OTHER INFORMATION: Construct based on miR30-based cassette with amiR5 active stem

<400> SEQUENCE: 181
gaaggtatat tgctgttgac agtgagcgta gtgataactc atagtacata gtgaagccac    60
agatgtatgt actatgagtt atcactatgc ctactgcctc gg                      102

<210> SEQ ID NO 182
<211> LENGTH: 104
<212> TYPE: DNA
<213> ORGANISM: Artificial Sequence
<220> FEATURE:
<223> OTHER INFORMATION: Construct based on miR30-based cassette with amiR6 active stem

<400> SEQUENCE: 182
gaaggtatat tgctgttgac agtgagcgcc gccatgtctg ttacgttaat agtgaagcca    60
cagatgtatt aacgtaacag acatggcggt gcctactgcc tcgg                    104

<210> SEQ ID NO 183
<211> LENGTH: 106
<212> TYPE: DNA
<213> ORGANISM: Artificial Sequence
<220> FEATURE:
<223> OTHER INFORMATION: Construct based on miR30-based cassette with amiR8 active stem

<400> SEQUENCE: 183
gaaggtatat tgctgttgac agtgagcgcg cagagagtgt tatattgcat tagtgaagcc    60
acagatgtaa tgcaatataa cactctctgc gtgcctactg cctcgg                  106

<210> SEQ ID NO 184
<211> LENGTH: 106
<212> TYPE: DNA
<213> ORGANISM: Artificial Sequence
<220> FEATURE:
<223> OTHER INFORMATION: Construct based on miR30-based cassette with amiR9 active stem

<400> SEQUENCE: 184
gaaggtatat tgctgttgac agtgagcgag gaattaaggt agaggttata tagtgaagcc    60
acagatgtat ataacctcta ccttaattcc ttgcctactg cctcgg                  106

<210> SEQ ID NO 185
<211> LENGTH: 104
<212> TYPE: DNA
<213> ORGANISM: Artificial Sequence
<220> FEATURE:
<223> OTHER INFORMATION: Construct based on miR30-based cassette with amiR10 active stem

<400> SEQUENCE: 185
gaaggtatat tgctgttgac agtgagcgag gcagagaagg gtatggaatt agtgaagcca    60
cagatgtaat tccataccct tctctgcctt gcctactgcc tcgg                    104

<210> SEQ ID NO 186
<211> LENGTH: 74
<212> TYPE: DNA

```
<213> ORGANISM: Artificial Sequence
<220> FEATURE:
<223> OTHER INFORMATION: Construct based on miR30-based cassette

<400> SEQUENCE: 186
cttgggaatg gcaaggcaca aagtgtgacc acatatttat gtggtcacac tttgtatctt      60
gctataccca gaaa                                                        74

<210> SEQ ID NO 187
<211> LENGTH: 70
<212> TYPE: DNA
<213> ORGANISM: Artificial Sequence
<220> FEATURE:
<223> OTHER INFORMATION: Construct based on miR30-based cassette

<400> SEQUENCE: 187
cttgggaatg gcaaggtaca ggatatgcga attaagaata attcgcatat cctgtctctt      60
gctataccca                                                             70

<210> SEQ ID NO 188
<211> LENGTH: 106
<212> TYPE: DNA
<213> ORGANISM: Artificial Sequence
<220> FEATURE:
<223> OTHER INFORMATION: Construct based on miR30-based cassette

<400> SEQUENCE: 188
gaaggtatat tgctgttgac agtgagcgaa agaacaatat cctactagtt tagtgaagcc      60
acagatgtaa actagtagga tattgttctt ctgcctactg cctcgg                    106

<210> SEQ ID NO 189
<211> LENGTH: 74
<212> TYPE: DNA
<213> ORGANISM: Artificial Sequence
<220> FEATURE:
<223> OTHER INFORMATION: Construct based on miR30-based cassette

<400> SEQUENCE: 189
cttgggaatg gcaaggttca acactgctta cgtctcctga cgtaagcagt gttgactctt      60
gctataccca gaaa                                                        74

<210> SEQ ID NO 190
<211> LENGTH: 127
<212> TYPE: DNA
<213> ORGANISM: Artificial Sequence
<220> FEATURE:
<223> OTHER INFORMATION: Construct based on miR30-based cassette

<400> SEQUENCE: 190
gaaggtatat tgctgttgac agtgagcgca cgctgggcgt taatcaaaga ctgtgaagcc      60
acagatgggt ctttgattaa cgcccagcgt tgcctactg cctcggactt caaggggcta     120
cttagg                                                               127

<210> SEQ ID NO 191
<211> LENGTH: 127
<212> TYPE: DNA
<213> ORGANISM: Artificial Sequence
<220> FEATURE:
<223> OTHER INFORMATION: Construct based on miR30-based cassette

<400> SEQUENCE: 191
gaaggtatat tgctgttgac agtgagcgca cgtctatatc atggccgaca ctgtgaagcc      60
```

```
acagatgggt gtcggccatg atatagacgt ttgcctactg cctcggactt caaggggcta    120
ctttagg                                                              127

<210> SEQ ID NO 192
<211> LENGTH: 127
<212> TYPE: DNA
<213> ORGANISM: Artificial Sequence
<220> FEATURE:
<223> OTHER INFORMATION: Construct based on miR30-based cassette

<400> SEQUENCE: 192
gaaggtatat tgctgttgac agtgagcgca cgtgacctat cccattacgg ctgtgaagcc    60
acagatgggc cgtaatggga taggtcacgt ttgcctactg cctcggactt caaggggcta   120
ctttagg                                                              127

<210> SEQ ID NO 193
<211> LENGTH: 79
<212> TYPE: DNA
<213> ORGANISM: Artificial Sequence
<220> FEATURE:
<223> OTHER INFORMATION: construct based on hsa-miR-484 cassette

<400> SEQUENCE: 193
agccucguuc aacacugcuu acgucuccua aaccccuaaa uagggacuuu cagagauguc    60
agcuugagcu uuuuuggcg                                                 79

<210> SEQ ID NO 194
<211> LENGTH: 79
<212> TYPE: DNA
<213> ORGANISM: Artificial Sequence
<220> FEATURE:
<223> OTHER INFORMATION: construct based on hsa-miR-484 cassette

<400> SEQUENCE: 194
agccucguac aggauaugcg aauuaagaaa aaccccuaaa uagggacuuu cccuuacuuu    60
gcacugugcu uuuuuggcg                                                 79

<210> SEQ ID NO 195
<211> LENGTH: 79
<212> TYPE: DNA
<213> ORGANISM: Artificial Sequence
<220> FEATURE:
<223> OTHER INFORMATION: construct based on hsa-miR-484 cassette

<400> SEQUENCE: 195
agccucgacc gucaugucug uuacguuaaa aaccccuaaa uagggacuuu ccaacgcaau    60
agaacgggcu uuuuuggcg                                                 79

<210> SEQ ID NO 196
<211> LENGTH: 106
<212> TYPE: DNA
<213> ORGANISM: Artificial Sequence
<220> FEATURE:
<223> OTHER INFORMATION: construct based on hsa-miR-143 cassette

<400> SEQUENCE: 196
gcgcagcgcc cugucuccca gccuaagaug ugacgaaggc agagcgguca guugggaguc    60
ccucugcauu cgucacaacu uaggaagaga gaaguuguuc ugcagc                  106

<210> SEQ ID NO 197
```

```
<211> LENGTH: 106
<212> TYPE: DNA
<213> ORGANISM: Artificial Sequence
<220> FEATURE:
<223> OTHER INFORMATION: construct based on hsa-miR-143 cassette

<400> SEQUENCE: 197
gcgcagcgcc cugucuccca gccuatgacc tatacgcgta attcagguca guugggaguc      60
agaauuaagc guauaggaca uaggaagaga gaaguuguuc ugcagc                    106

<210> SEQ ID NO 198
<211> LENGTH: 106
<212> TYPE: DNA
<213> ORGANISM: Artificial Sequence
<220> FEATURE:
<223> OTHER INFORMATION: construct based on hsa-miR-143 cassette

<400> SEQUENCE: 198
gcgcagcgcc cugucuccca gccuugggag uacagacgau gcaaagguca guugggaguc      60
auugcauugu cuguacugcc aaggaagaga gaaguuguuc ugcagc                    106

<210> SEQ ID NO 199
<211> LENGTH: 82
<212> TYPE: DNA
<213> ORGANISM: Artificial Sequence
<220> FEATURE:
<223> OTHER INFORMATION: construct based on hsa-miR-99a cassette

<400> SEQUENCE: 199
cccauuggca uauucaacac cugcuuacgu cuuccuguga aguggaccga ggagauguau      60
ccaguguuga cugugucagu gu                                              82

<210> SEQ ID NO 200
<211> LENGTH: 82
<212> TYPE: DNA
<213> ORGANISM: Artificial Sequence
<220> FEATURE:
<223> OTHER INFORMATION: construct based on hsa-miR-99a cassette

<400> SEQUENCE: 200
cccauuggca uauacaggau augcgaauua agaagugaag uggaccguuc uuaguuccga      60
uauccuguca gugugucagu gu                                              82

<210> SEQ ID NO 201
<211> LENGTH: 82
<212> TYPE: DNA
<213> ORGANISM: Artificial Sequence
<220> FEATURE:
<223> OTHER INFORMATION: construct based on hsa-miR-99a cassette

<400> SEQUENCE: 201
cccauuggca uaccgucau gucuguuacg uuaagugaag uggaccguua acggaacuca       60
caugacggca gugugucagu gu                                              82

<210> SEQ ID NO 202
<211> LENGTH: 109
<212> TYPE: DNA
<213> ORGANISM: Artificial Sequence
<220> FEATURE:
<223> OTHER INFORMATION: construct based on hsa-miR-181c cassette

<400> SEQUENCE: 202
cggaaaauuu gccaagggau ugggguuca acacugcuua cgucuccuuu ggcagcuca       60
```

```
ggcaaagaga cguaccagug uugguccuga ggccuggaau ugccauccu            109

<210> SEQ ID NO 203
<211> LENGTH: 109
<212> TYPE: DNA
<213> ORGANISM: Artificial Sequence
<220> FEATURE:
<223> OTHER INFORMATION: construct based on hsa-miR-181c cassette

<400> SEQUENCE: 203
cggaaaauuu gccaaggguu uggggguaca ggauaugcga auuaagaauu gggcagcuca    60
ggcaauuuua auucuauauc cugguccuga ggccuggaau ugccauccu              109

<210> SEQ ID NO 204
<211> LENGTH: 109
<212> TYPE: DNA
<213> ORGANISM: Artificial Sequence
<220> FEATURE:
<223> OTHER INFORMATION: construct based on hsa-miR-181c cassette

<400> SEQUENCE: 204
cggaaaauuu gccaaggguu uggggggaccg ucaugucugu uacguuaauu gggcagcuca   60
ggcaauuacg uaaccacaug acguaccuga ggccuggaau ugccauccu              109

<210> SEQ ID NO 205
<211> LENGTH: 71
<212> TYPE: DNA
<213> ORGANISM: Artificial Sequence
<220> FEATURE:
<223> OTHER INFORMATION: construct based on hsa-miR-199a1 cassette

<400> SEQUENCE: 205
gccaauggca ucucggcuag aaccacucag gaggcucuca auguguguu ucuagccuag     60 augcccaagg c                                                        71

<210> SEQ ID NO 206
<211> LENGTH: 71
<212> TYPE: DNA
<213> ORGANISM: Artificial Sequence
<220> FEATURE:
<223> OTHER INFORMATION: construct based on hsa-miR-199a1 cassette

<400> SEQUENCE: 206
gccaauuccu auaugcuuaa uuccuuucag gaggcucuca auguguaaga auuaagcgua    60
uaggacaagg c                                                        71

<210> SEQ ID NO 207
<211> LENGTH: 71
<212> TYPE: DNA
<213> ORGANISM: Artificial Sequence
<220> FEATURE:
<223> OTHER INFORMATION: construct based on hsa-miR-199a1 cassette

<400> SEQUENCE: 207
gccaaucagu acauacaaug cacauuucag gaggcucuca auguguaauu gcauugucug    60
uacugccagg c                                                        71
```

MICRORNA-BASED COMPOSITIONS AND METHODS USED IN DISEASE TREATMENT

FIELD

The present disclosure relates to microRNA compositions and methods used in treating disease.

BACKGROUND

The following paragraph is not an admission that anything discussed herewith is prior art or part of the knowledge of persons skilled in the art.

A microRNA (abbreviated miRNA) is a small non-coding RNA molecule that functions in RNA silencing and post-transcriptional regulation of gene expression. The ability of miRNAs to regulate gene expression illustrates their potential as a therapeutic.

INTRODUCTION

The following introduction is intended to introduce the reader to this specification but not to define any invention. One or more inventions may reside in a combination or sub-combination of the apparatus elements or method steps described below or in other parts of this document. The inventors do not waive or disclaim their rights to any invention or inventions disclosed in this specification merely by not describing such other invention or inventions in the claims.

Viral therapy is a field where specific viruses have been selected or genetically manipulated to treat disease, either by prophylaxis, such as vaccines, or through viral therapy, such as gene therapy or oncolytic viruses. Viruses such as vesicular stomatitis virus (VSV), Vaccinia, and herpes simplex virus (HSV) can be modified for use as vaccine backbones or in therapeutic applications, such as gene therapy or oncolytic viral therapy.

Oncolytic viruses (OVs) are viruses used to specifically infect, replicate in, and kill malignant cells, leaving normal tissues unaffected. Several OVs, such as VSV, have reached advanced stages of clinical evaluation for the treatment of various neoplasms.

Although viral therapy is a promising therapeutic strategy, antiviral responses raised by a patient treated with a virus may reduce the therapeutic effectiveness of the virus. Without wishing to be bound by theory, the authors of the present disclosure believe that exemplary miRNAs according to the present disclosure, when encoded by a virus, are produced and released from the infected cell in extracellular vesicles (EV) (cell-derived membranous structures, including exosomes and microvesicles), regulating gene expression in uninfected cells to enhance the therapeutic effectiveness of the virus in the patient. The authors believe that the released extracellular vesicles can circulate in the patient and affect distant cells. In one aspect, the present disclosure provides a miRNA hairpin encoded by a virus that, when processed by a virus-infected cell, increases the therapeutic effectiveness of the virus. In the context of the present disclosure, such a miRNA hairpin may be referred to as a "therapy-enhancing miRNA hairpin". In some examples, the present disclosure provides a virus whose genome includes a nucleotide sequence that encodes at least one miRNA hairpin that enhances the therapeutic effectiveness of the virus. In other examples, the present disclosure provides a plasmid for modifying a genome of a target virus, where the plasmid includes a sequence that, when inserted into the target virus, encodes a miRNA hairpin that enhances the therapeutic effectiveness of the virus.

The authors of the present disclosure have also identified pre-miRNA and pri-miRNA that, when processed by a virus-infected cell, increase EV secretion of the encoded miRNA hairpin by the virus-infected cell. In the context of the present disclosure, such a pre-miRNA or pri-miRNA may be referred to as "an EV-directing pre-miRNA" or "an EV-directing pri-miRNA", respectively. In another aspect of the present disclosure, the disclosure provides a pre-miRNA or pri-miRNA including a miRNA hairpin that, when processed by an virus-infected cell, increases secretion of the encoded miRNA hairpin via EVs expressed by the virus-infected cell. The pre-miRNA or pri-miRNA may be referred to as an "EV-directing cassette". In some examples, the present disclosure provides a virus whose genome includes a nucleotide sequence that encodes a pre-miRNA or pri-miRNA that increases EV secretion of the miRNA hairpin. The present disclosure also provides a method of identifying an EV-directing pre-miRNA or pri-miRNA for an oncolytic virus. The present disclosure also provides a plasmid for modifying a genome of a target virus, where the plasmid includes a sequence that, when inserted into the target virus, encodes an EV-directing pre-miRNA or an EV-directing pri-miRNA.

In one aspect, the present disclosure provides a miRNA-hairpin for encoding by a virus that, when processed by a virus-infected cell, increases the therapeutic effectiveness of the virus.

The miRNA-hairpin may include:

- a sense sequence that is at least 60% identical to SEQ ID NO: 1 and at least 70% identical over the middle seven nucleotides of SEQ ID NO: 1, and an antisense sequence that is at least 60% identical to SEQ ID NO: 2 and at least 70% identical over the middle seven nucleotides of SEQ ID NO: 2;
- a sense sequence that is at least 60% identical to SEQ ID NO: 3 and at least 70% identical over the middle seven nucleotides of SEQ ID NO: 3, and an antisense sequence that is at least 60% identical to SEQ ID NO: 4 and at least 70% identical over the middle seven nucleotides of SEQ ID NO: 4;
- a sense sequence that is at least 60% identical to SEQ ID NO: 5 and at least 70% identical over the middle seven nucleotides of SEQ ID NO: 5, and an antisense sequence that is at least 60% identical to SEQ ID NO: 6 and at least 70% identical over the middle seven nucleotides of SEQ ID NO: 6;
- a sense sequence that is at least 60% identical to SEQ ID NO: 7 and at least 70% identical over the middle seven nucleotides of SEQ ID NO: 7, and an antisense sequence that is at least 60% identical to SEQ ID NO: 8 and at least 70% identical over the middle seven nucleotides of SEQ ID NO: 8;
- a sense sequence that is at least 60% identical to SEQ ID NO: 9 and at least 70% identical over the middle seven nucleotides of SEQ ID NO: 9, and an antisense sequence that is at least 60% identical to SEQ ID NO: 10 and at least 70% identical over the middle seven nucleotides of SEQ ID NO: 10;
- a sense sequence that is at least 60% identical to SEQ ID NO: 11 and at least 70% identical over the middle seven nucleotides of SEQ ID NO: 11, and an antisense sequence that is at least 60% identical to SEQ ID NO: 12 and at least 70% identical over the middle seven nucleotides of SEQ ID NO: 12;

a sense sequence that is at least 60% identical to SEQ ID NO: 13 and at least 70% identical over the middle seven nucleotides of SEQ ID NO: 13, and an antisense sequence that is at least 60% identical to SEQ ID NO: 14 and at least 70% identical over the middle seven nucleotides of SEQ ID NO: 14; or a sense sequence that is at least 60% identical to SEQ ID NO: 15 and at least 70% identical over the middle seven nucleotides of SEQ ID NO: 15, and an antisense sequence that is at least 60% identical to SEQ ID NO: 16 and at least 70% identical over the middle seven nucleotides of SEQ ID NO: 16.

The miRNA-hairpin may include a loop sequence according to SEQ ID NO: 17.

In another aspect, the present disclosure provides a virus whose genome includes a nucleic acid sequence that encodes at least one miRNA-hairpin according to the present disclosure.

In still another aspect, the present disclosure provides a plasmid that comprises a nucleotide sequence that, when inserted into a virus, encodes at least one miRNA hairpin according to the present disclosure.

In yet another aspect, the present disclosure provides a cassette encoded by a virus that, when processed by a cell that is infected by the virus, increases extracellular vesicle secretion of at least one miRNA hairpin encoded by the cassette.

The cassette may include at least one sequence according to: [Z]-[A]-[X]-[Y]-[X']-[B]-[Z'], wherein [Z] and [Z'] represent optional flanking sequences; [X] and [X'] represent sense and antisense sequences of the miRNA hairpin stem; [Y] represents a loop sequence of the miRNA hairpin; and [A] and [B] represent, respectively: sequences that are up to 5 nucleotides different from SEQ ID NOs: 20 and 21; 23 and 24; 27 and 28; 30 and 31; 33 and 34; 36 and 37; 39 and 40; 42 and 43; 45 and 46; 48 and 49; 51 and 52; 54 and 55; 57 and 58; 60 and 61; 63 and 64; 66 and 67; 69 and 70; 72 and 73; 75 and 76; 78 and 79; 81 and 82; 84 and 85; 87 and 88; 90 and 91; 93 and 94; 96 and 97; 99 and 100; 102 and 103; 105 and 106; 108 and 109; 111 and 112; 114 and 115; 117 and 118; 120 and 121; 123 and 124; 126 and 127; 129 and 130; 132 and 133; 135 and 136; 138 and 139; 141 and 142; 144 and 145; 147 and 148; 150 and 151; or 153 and 154. When the cassette includes more than one sequence according to: [Z]-[A]-[X]-[Y]-[X']-[B]-[Z'], each sequence is independently selected.

[A] and [B] may represent sequences that are identical to the sequences identified by SEQ ID NO.

[Z] and [Z'] may be present and have sequences that are at least 80% identical to SEQ ID NOs: 18 and 19, respectively.

[Y] may have a sequence that is at least 80% identical to SEQ ID NO: 17.

In still another aspect, the present disclosure provides a virus whose genome comprises a nucleotide sequence that encodes one or more cassettes according to the present disclosure. The one or more cassettes may encode 2, 3, 4, 5, 6, 7, 8, 9, 10, 11, 12, 13, 14, 15, 16, 17, 18, 19, 20, or more than 20, such as about 30, about 40, about 50, about 60, about 70, about 80, about 90, or about 100, independently selected sequences according to [Z]-[A]-[X]-[Y]-[X']-[B]-[Z']. A virus with a larger genome may have a greater capacity for modification, and may therefore include more cassettes and/or more encoded sequences, than a virus with a smaller genome.

In an further aspect, the present disclosure provides a plasmid that includes a nucleotide sequence that, when inserted into a virus, encodes one or more cassettes according to the present disclosure.

In yet still another aspect, the present disclosure provides a plasmid that includes one or more, independently selected, nucleotide sequences according to any one of SEQ ID NOs: 178-207.

In another aspect, the present disclosure provides an oncolytic virus whose genome includes one or more, independently selected, nucleotide sequences according to any one of SEQ ID NOs: 178-207.

BRIEF DESCRIPTION OF THE DRAWINGS

Embodiments of the present disclosure will now be described, by way of example only, with reference to the attached Figures.

Figures 1, 2:
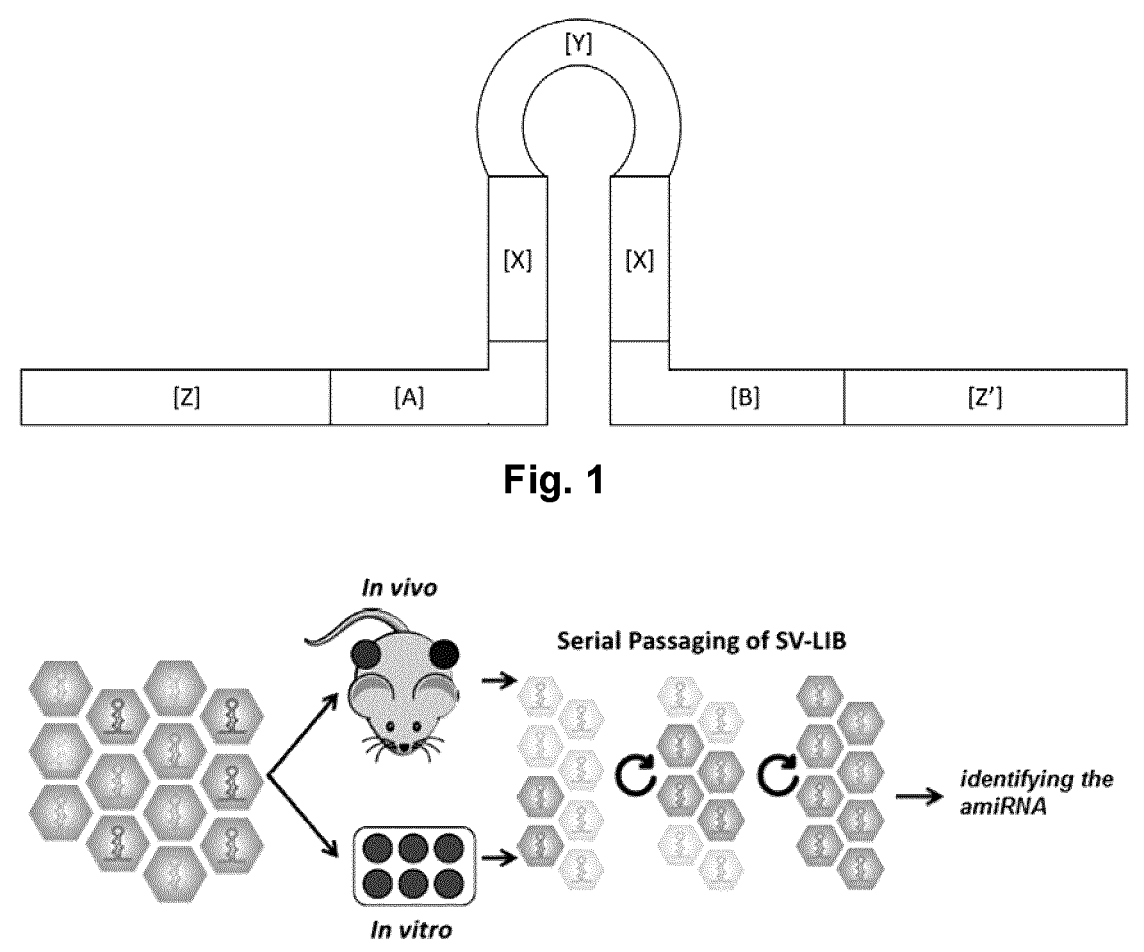

FIG. 1 is an illustration of a general construct according to the present disclosure.

FIG. 2 is an illustration of a strategy used to identify therapy-enhancing miRNA hairpins.

FIG. 3 is an illustration of a genome of a rhabdovirus that includes a nucleotide sequence that encodes a miRNA hairpin. The encoding sequence is illustrated as a cassette in a stem-loop configuration, where the cassette encodes the miRNA hairpin.

FIG. 4 is a Kaplan-Meier survival curve showing mortality of mice bearing orthotopic pancreatic tumors treated with VSV-amiR6, an exemplary virus of the present disclosure.

FIG. 5 is an illustration of a strategy used to demonstrate that a therapy-enhancing miRNA hairpin according to the present disclosure is expressed and loaded in EVs budded from a virus infected cancer cell.

FIG. 6 is a Kaplan-Meier survival curve showing mortality of mice bearing intraperitoneal melanoma tumors treated with VSV-amiR6.

FIG. 7 is an illustration of a strategy used to identify EV-directing pre-miRNA.

FIG. 8 is an illustration showing three miRNA hairpin cassettes cloned in tandem from a single viral promoter.

FIG. 9 is an illustration showing three miRNA hairpin cassettes cloned in tandem with separate viral promoters.

DEFINITIONS

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The use of the word "a" or "an" when used in conjunction with the term "comprising" in the claims and/or the specification may mean "one," but it is also consistent with the meaning of "one or more," "at least one," and "one or more than one."

As used in this specification and claim(s), the expressions "a sequence that encodes a miRNA" and "a sequence that encodes a miRNA hairpin" (and similar expressions) refers to a DNA or RNA sequence that, when processed by a cell, generates the miRNA or miRNA hairpin. The encoding sequence may be, for example: a portion of the genome of a DNA virus, a portion of the genome of an RNA virus, a pri-miRNA sequence or a pre-miRNA sequence. Depending on the nature of the sequence that encodes the miRNA or miRNA hairpin, the encoding sequence may include a sequence that is (i) identical to the miRNA or miRNA hairpin sequence, (ii) complementary to the miRNA or miRNA hairpin sequence, or (iii) reverse complementary to the miRNA or miRNA hairpin sequence. A sequence that encodes pre-miRNA or pri-miRNA may be referred to as a "cassette".

In the context of the present disclosure, it should be understood that discussions of a plurality of items, such as nucleotide sequences, cassettes, miRNA hairpins, do not require that each item be identical to the other items. For example, a plasmid that encodes "at least one nucleotide sequence that is at least 90% identical to SEQ ID NO: #" refers to, among other things: a plasmid that encodes a single copy of the nucleotide sequence SEQ ID NO: #"; a plasmid that encodes multiple copies of the nucleotide sequence SEQ ID NO: #"; and a plasmid that encodes a plurality of different nucleotide sequences, all of which being at least 90% identical to SEQ ID NO: #. The expression "independently selected" refers to one item of a group not influencing the selection of any of the other items in the group. In the above example, each of the plurality of different nucleotides is independently selected.

DETAILED DESCRIPTION

It will be appreciated that embodiments and examples are provided for illustrative purposes intended for those skilled in the art, and are not meant to be limiting in any way.

In one aspect, the present disclosure provides a miRNA hairpin that, when processed by a virus-infected cell, increases the therapeutic effectiveness of the virus. As noted above, such a miRNA hairpin may be referred to as a "therapy-enhancing miRNA hairpin". A virus according to this aspect of the present disclosure has a genome that includes at least one nucleotide sequence that encodes a therapy-enhancing miRNA hairpin.

In the context of the present disclosure, increasing or enhancing the therapeutic effectiveness of a virus may include: enhancing cytotoxicity of the virus, enhancing replication in vivo of the virus, sensitizing an OV-infected cancer cell or a non-infected tumor cell to a chemotherapeutic or other drug (such as a small molecule inhibitor), inducing cytotoxicity of an OV-infected cancer or tumor cell or a non-infected cancer or tumor cell, reducing a neutralizing antibody response to the OV, an enhanced ability to stimulate the immune system, or any combination thereof. In some instances, the non-infected cell may be the same cell type as the infected cell or a different type of cell. It should be understood that "tumor cell" refers to any cell found within a tumor, even if the cell is not cancerous.

The therapeutic effectiveness of an OV may be increased in a cancer cell, such as, but not limited to: HPAC (human pancreatic adenocarcinoma), MiaPaCa-2 (human pancreas carcinoma), Panc02 (mouse pancreatic ductal adenocarcinoma), PanC1 (human pancreas epithelioid carcinoma), 786-O (human kidney renal cell adenocarcinoma), HPAF II (human pancreas adenocarcinoma), BxPC3 (human pancreas adenocarcinoma), SKOV3 (human ovarian cancer), cancer-associated fibroblasts (e.g. PCa-CAF), patient-derived cells or any combination thereof.

A miRNA hairpin includes a stem portion and a loop portion according to the established principles in miRbase.org, as recognized in the art. The stem portion is formed from the at least partial pairing of a "sense" sequence and an "anti-sense" sequence. The two sequences are joined by a loop portion (which may also be referred to herein as a loop sequence). The loop portion and part of the stem may be cleaved during cellular processing. The sense and anti-sense sequences form a double stranded miRNA duplex. The double stranded miRNA duplex separates to form at least one single stranded RNA. The single stranded RNA may act to silence or post-transcriptionally regulate expression of one or more genes.

A therapy-enhancing miRNA hairpin according to the present disclosure may include a sense sequence and an anti-sense sequence, as shown in Table 1. The therapy-enhancing miRNA hairpin also includes a loop portion joining the two sequences. The loop portion may be from 3 to 50 nucleotides in length.

In the context of the present disclosure, reference to a hairpin according to "amiR[#]" refers to a hairpin that includes the sense and the anti-sense sequences as shown in Table 1. For example, the artificial miRNA hairpin "amiR1" includes a sequence according to SEQ ID NO: 1 and a sequence according to SEQ ID NO: 2, where SEQ ID NO: 1 and SEQ ID NO: 2 are joined by a sequence defining the loop portion.

TABLE 1

List of artificial microRNAs (amiRs).

| Reference | Sense and anti-sense sequences of the stem portion of a therapy-enhancing miRNA hairpin | SEQ ID NO: |
|---|---|---|
| amiR1 | ACCAACATGTCTCTTCTCCTAT | 1 |
|  | ATAGGAGAAGAGACATGTTGGT | 2 |
| amiR2 | TTGTCTTATTCTTTAATAACAT | 3 |
|  | ATGTTATTAAAGAATAAGACAA | 4 |
| amiR3 | TTGTCTTACTCTTCAATAACAT | 5 |
|  | ACCAACATGTCTCTTCTCCTAT | 6 |
| amiR5 | TAGTGATAACTCATAGTACA | 7 |
|  | TGTACTATGAGTTATCACTA | 8 |
| amiR6 | CCGCCATGTCTGTTACGTTAA | 9 |
|  | TTAACGTAACAGACATGGCGG | 10 |
| amiR8 | CGCAGAGAGTGTTATATTGCAT | 11 |
|  | ATGCAATATAACACTCTCTGCG | 12 |
| amiR9 | AGGAATTAAGGTAGAGGTTATA | 13 |
|  | TATAACCTCTACCTTAATTCCT | 14 |
| amiR10 | AGGCAGAGAAGGGTATGGAAT | 15 |
|  | ATTCCATACCCTTCTCTGCCT | 16 |

A therapy-enhancing miRNA hairpin according to the present disclosure may include a sequence that is: (a) at least 60% identical (such as at least 70%, at least 80%, or at least 90% identical) to any one of SEQ ID NO: 1-16 and (b) at least 70% identical (such as at least 85% identical) over the middle seven nucleotides of the reference sequence. That is, at least five of the seven middle nucleotides are identical to the reference sequence. Such a miRNA hairpin may be referred to as a "variant" of the corresponding amiR. The authors note that SEQ ID NO: 3 is 91% identical to SEQ ID NO: 5, and the middle seven nucleotides are identical to five of the middle seven nucleotides of SEQ ID NO: 5 (that is, they are about 71% identical over the middle seven nucleotides). Without wishing to be bound by theory, the authors of the present disclosure believe that the middle seven nucleotides may be more active in gene regulation. On that basis, it may be desirable for the sequence to be 100% identical over the middle seven nucleotides of the reference sequence. For example, a therapy-enhancing miRNA hairpin according to the present disclosure may include a sequence that is 60% identical to SEQ ID NO: 9 while being 100% identical over the middle seven nucleotides of SEQ ID NO: 9; and a sequence that is 100% identical to SEQ ID NO: 10, with the two sequences being joined by a loop sequence. Such a miRNA hairpin may be referred to as a variant of amiR6.

One example of a loop sequence that may be used in a therapy-enhancing miRNA hairpin of any one of amiRs 1-10, or a variant thereof, is:

(SEQ ID NO: 17)
UAGUGAAGCCACAGAUGUA.

Therapy-enhancing miRNA hairpins are processed by the virus-infected cell to cleave the loop portion and part of the stem of the hairpin, generating one single-stranded RNA with a "sense" sequence and one single-stranded RNA with an "anti-sense" sequence.

A virus according to the present disclosure may encode more than one therapy-enhancing miRNA hairpin according to the present disclosure. For example, a virus may include (i) a nucleotide sequence that encodes a hairpin that includes SEQ ID NOs: 9 and 10, as well as (ii) a nucleotide sequence that encodes a hairpin that includes SEQ ID NOs: 11 and 12. The virus may encode: (a) multiple therapy-enhancing miRNA hairpins in tandem with a single promoter, (b) multiple therapy-enhancing miRNA hairpins each having their own promoter; or (c) a combination thereof.

Therapy-enhancing miRNA hairpins are encoded within a pri-miRNA or a pre-miRNA. The sequence encoding the pre-miRNA or pri-miRNA may be referred to as a "therapy-enhancing cassette". The virus-infected cell processes the pre-miRNA or pri-miRNA to produce the therapy-enhancing miRNA hairpin. A virus that encodes a therapy-enhancing miRNA hairpin according to the present disclosure may additionally include sequences in the genome defining linkers or restriction sites adjacent to the sequence encoding the pre-miRNA or pri-miRNA.

A virus encoding a therapy-enhancing miRNA hairpin according to the present disclosure may include in its genome a cassette including a sequence as shown in Appendix A. Infection of a cell with a virus that includes a cassette having "cassette sequence amiR[#]" results in a virus-infected cell that produces a miRNA hairpin according to amiR[#]. For example, infection of a cell with a virus that includes a cassette having "cassette sequence amiR6" results in a virus-infected cell that produces a miRNA hairpin with nucleotides that include SEQ ID NO: 9 and 10.

The therapy-enhancing miRNA hairpin may be encoded by an otherwise wild-type virus, or by a variant of a wild-type virus. The virus may be, for example: Vesicular Stomatitis Virus (VSV), Vaccinia virus, Maraba virus, herpes simplex virus (HSV), Farmington virus, Carajas virus, Muir Springs virus, Bahia grande virus, or a variant thereof.

A variant of a wild-type oncolytic virus or other virus may have: one or more genetic mutations resulting in non-wild type sequences of one or more of the viral gene products; a pseudotyped gene; additional nucleotide sequences that encode one or more biomolecules; a deletion of a gene; an interruption of a gene; a truncation of a gene; or any combination thereof. The genetic changes may confer to the variant virus: increased cytotoxicity, attenuation in non-cancerous cells, enhanced infection rate, enhanced replication rate, enhanced growth in cancerous cells, enhanced ability to stimulate the immune system, or any combination thereof. It should be understood that reference to "enhanced", "increased" or "reduced" is in comparison to the corresponding wild-type virus. One specific example of such a variant oncolytic virus is: a variant of HSV-1 that: (i) lacks a gene encoding Infected Cell Protein 34.5 (ICP34.5), (ii) lacks a gene encoding Infected Cell Protein 47 (ICP47), and (iii) includes a gene encoding human Granulocyte-macrophage colony-stimulating factor (GM-CSF). Such a variant is disclosed by BL Liu et al. in Gene Therapy (2010) 10, 292-303.

The nucleotide sequence that encodes the therapy-enhancing miRNA hairpin may be inserted anywhere in the genomic backbone of the virus so long as the encoding sequence does not interfere with the production of the vital viral gene products. For example: rhabdoviruses include coding sequences for five proteins in the order 5'-N-P-M-G-L-3'; and the nucleotide sequence may be inserted between the N and the P genes, between the P and the M genes, or between the G and the L genes. In viruses whose genes include non-coding introns, or in viruses whose genomes include non-vital genes, the nucleotide sequence may be inserted within a gene. HVS and Vaccinia virus are examples of viruses that include non-vital genes.

In another aspect, the present disclosure provides a pre-miRNA that, when expressed by a virus-infected cell, increases EV secretion of the encoded miRNA hairpin by the virus-infected cell. As noted above, such pre-miRNA may be referred to as "an EV-directing pre-miRNA". The increase in EV secretion of a miRNA hairpin is relative to the amount of the miRNA hairpin secreted in EVs of a virus-infected cell that does not express an EV-directing pre-miRNA or EV-directing pri-miRNA that encodes the miRNA hairpin. An EV-directing pre-miRNA may originate from a cellular miRNA or a virally expressed miRNA. An EV-directing pre-miRNA or pri-miRNA according to the present disclosure may result in about at least a 40-fold increase in EV secretion of the encoded miRNA hairpin for cellular derived miRNA hairpins (Table 2 to Table 4), or at least about 2-fold increase for viral derived miRNA hairpins (Table 5).

In the following tables, exemplary constructs of EV-directing pre-miRNA are illustrated. In the exemplary constructs, stem structure sequences [A] and [B] represent sequences of the pre-miRNA that affect EV secretion, [X] and [X'] represent the sense and anti-sense sequences of the miRNA hairpin stem encoded by the pre-miRNA or pri-miRNA. These sequences are joined by a loop portion, designated [Y]. The loop portion, as part of the secondary structure, may additionally affect EV secretion. The [X] and [X'] sequences are flanked by the stem structure sequences [A] and [B], which are optionally further flanked by flanking sequences [Z] and [Z'] respectively. The illustrated constructs, depicted in FIG. 1, form single amino acid chain sequences according to the following formula: [Z]-[A]-[X]-

[Y]-[X']-[B]-[Z'], where [Z] and [Z'] are optional. The miR secondary structure is formed during cellular processing, with the [A] and [X] sense sequences forming a double stranded miRNA duplex with the [X'] and [B] anti-sense sequences, which thereby form a loop structure from the adjoining loop portion [Y].

Although the illustrated constructs identify specific loop sequences [Y], it should be understood that specific constructs could have alternative loop sequences or loop sequences from another illustrated construct.

In some embodiments, the [A] and [B] sequences do not have any nucleotides, and are therefore omitted. In such embodiments, the loop portion affects EV secretion. Additional nucleotides, such as up to five nucleotides, may be included between any adjacent portions. These additional nucleotides may be used to encourage the formation of a secondary structure that more closely mimics the secondary structure of the wild-type pre-miRNA.

The optional flanking sequences [Z] and [Z'] may be from 3 to 400 nucleotides in length. If present, the flanking sequences [Z] and [Z'] may include, respectively, sequences that are: at least 80% identical to GAAGGTATAT-TGCTGTTGACAGTGAGCG (SEQ ID NO: 18) and at least 80% identical to TGCCTACTGCCTCGG (SEQ ID NO: 19). The optional flanking sequences [Z] and [Z'] in a pre-miRNA may be at least 80% identical to sequences derived from the pri-miRNA sequences of the corresponding wild-type pre-miRNA, the sequences of which are available from publicly available databases. An EV-directing pre-miRNA or an EV-directing pri-miRNA according to the present disclosure may include a sequence that is at least 80% identical to a sequence shown in the tables.

It should be understood that the sense and anti-sense sequences of an EV-directing pre-miRNA are sufficiently complementary for the two sequences to participate in the stem portion of the pre-miRNA hairpin even if the sense sequence includes one or more nucleotides that do not pair with nucleotides in the anti-sense sequence. The sense and anti-sense sequences do not need to be fully complementary. For example, the sense and anti-sense sequences may include non-complementary pairs or additional nucleotides on either the [X] or [X'] sequence creating a bubble within the stem portion of the hairpin.

Similarly, it should be understood that various pairs of sequences shown in Table 2 to Table 5 include portions that do not pair. For example, SEQ ID NO: 20 is not fully complementary to SEQ ID NO: 21 since SEQ ID NO: 20 includes 10 nucleotides that do not pair with nucleotides in SEQ ID NO: 21. Without wishing to be bound by theory, the authors believe that the secondary structure conferred by the paired and unpaired nucleotides in a miR stem-loop sequence influence the ability for the pre-miRNA to direct the miRNA hairpin to the EV. On this basis, it may be desirable for an EV-directing pre-miRNA, whose sequence is not 100% identical to a sequence shown in the tables, to maintain the number and location of the paired and unpaired nucleotides. For example, an EV-directing pre-miRNA or cassette according to the present disclosure may have a sequence that is 80% identical to the 26 nucleotides of SEQ ID NO: 20, with the 5 different nucleotides maintaining the paired/unpaired relationship with the corresponding nucleotides of the complementary strand. The number and location of paired and unpaired nucleotides of a miR stem-loop sequence secondary structure may be identified through a search of the name of the originating miRNA stem-loop on any online data base, such as www.mirbase.org.

The [X] and [X'] sequences of any one of the exemplary constructs may be replaced with sequences of 18 to 23 nucleotides corresponding to sequences of naturally occurring mature miRNA, artificially designed mature miRNAs, anti-miRNA, short hairpin RNA (shRNA), or small interfering RNA. For example, the [X] and [X'] sequences of any one of the exemplary constructs may be replaced with sequences that form a therapy-enhancing miRNA hairpin according to the present disclosure. For example, [X] and [X'] sequences may be replaced with SEQ ID NOs: 1 and 2; SEQ ID NOs: 8 and 9; or a sequence that is at least 60% identical to SEQ ID NO: 3 while being 100% identical over the middle seven nucleotides of SEQ ID NO: 3, and a sequence that is 100% identical to SEQ ID NO: 4.

An EV-directing pre-miRNA cassette may include a sequence as shown in Table 2, or a variant sequence where the [A] and [B] sequences each include up to 5 different nucleotides to maintain the originating pri-miR's secondary structure. Although the nucleotide sequences refer to [Z] and [Z'], these are optional and may not be present. The fold increase reflects a measured increase in mature miRNA encoded by the wild-type pre-miRNA sequence in EVs derived from tumor cells infected by VSV.

TABLE 2

| Cellular miRNAs enriched more than 40-fold in EVs after VSV infection. | | | |
|---|---|---|---|
| Nucleotide sequence (name of originating miR stem-loop sequence) | SEQ ID Nos for [A], [B] | Exemplary loop sequence (SEQ ID NO) | fold increase in EVs observed |
| [Z]-GCGCAGCGCCCUGUCUCCCAGCCU-[X]-[Y]-[X']-AGGAAGAGAGAAGUUGUUCUGCAGC-[Z'] (hsa-miR-143) | 20, 21 | CAGUUGGGAGU (22) | 127 |
| [Z]-CCCAUUGGCA-[X]-[Y]-[X']-UGUCAGUGUG-[Z'] (hsa-miR-99a) | 23, 24 | GUGAAGUGGACCGCA (25) | 89 |
| [Z]-[X]-[Y]-[X']-[Z'] (hsa-miR-3928) | | GGGCAGGAAGC (26) | 89 |
| [Z]-CUCCCCAUGGCC-[X]-[Y]-[X']-GGACCUGGGGAC-[Z'] (hsa-miR-150) | 27, 28 | CUGGGCUCAGACC (29) | 85 |

TABLE 2-continued

Cellular miRNAs enriched more than 40-fold in EVs after VSV infection.

| Nucleotide sequence (name of originating miR stem-loop sequence) | SEQ ID Nos for [A], [B] | Exemplary loop sequence (SEQ ID NO) | fold increase in EVs observed |
| --- | --- | --- | --- |
| [Z]-CUUGGGAAUGGCAAGG-[X]-[Y]-[X']-UCUUGCUAUACCCAGA-[Z']<br>(hsa-miR-451a) | 30, 31 | AGUU<br>(32) | 85 |
| [Z]-GAGUUUGGUUUUGUUUGGGUUUG-[X]-[Y]-[X']-CCAACCUAAGCUC-[Z']<br>(hsa-miR-331) | 33, 34 | CAGAUCAAACCAG<br>(35) | 85 |
| [Z]-UUGAAG-[X]-[Y]-[X']-UCUCAG-[Z']<br>(hsa-miR-369) | 36, 37 | UUUAUUGACUUCG<br>(38) | 80 |
| [Z]-ACCAAGUUUCAGUU-[X]-[Y]-[X']-AGCUGACUUGGA-[Z']<br>(hsa-miR-30b) | 39, 40 | GUAAUACAUGGAUUGG<br>(41) | 80 |
| [Z]-GAUACUCGAAGGA-[X]-[Y]-[X']-UUUUUAGUAUC-[Z']<br>(hsa-miR-494) | 42, 43 | UUAUUUAUGA<br>(44) | 71 |
| [Z]-AAGAUCCUGCUG-[X]-[Y]-[X']-CAGCAGGAUUCUCC-[Z']<br>(hsa-miR-1305) | 45, 46 | UAUUGUAAAGAUAC<br>(47) | 66 |
| [Z]-CU-[X]-[Y]-[X']-AA-[Z']<br>(hsa-miR-362) | 48, 49 | GCUAUUUCAGUGC<br>(50) | 56 |
| [Z]-CCGCCCCGGGCCGCGGCU-[X]-[Y]-[X']-AGCCGCCGCCCCCAAACCUCGAGCGGG-[Z']<br>(hsa-miR-219a-1) | 51, 52 | CGAGUCUAUGGCUCCGGCCG<br>(53) | 56 |
| [Z]-GACAGUGCAGUCA-[X]-[Y]-[X']-UGAGUGUACUGUG-[Z']<br>(hsa-miR-142) | 54, 55 | AACAGCACUGGAGGG<br>(56) | 52 |
| [Z]-UUGGGCA-[X]-[Y]-[X']-UACUCGGUC-[Z']<br>(hsa-miR-744) | 57, 58 | GUCUUACUGAAGGUUUCCUGGAAACCACGCACAUG<br>(59) | 52 |
| [Z]-ACGGCAUCUUUGC-[X]-[Y]-[X']-GGUAAGGACGGCUGU-[Z']<br>(hsa-miR-3619) | 60, 61 | CCGUGGUGG<br>(62) | 52 |
| [Z]-GUGUCUCUCU-[X]-[Y]-[X']-UGAGGGAACAC-[Z']<br>(hsa-miR-4725) | 63, 64 | CACCAGGGAGCUUUCCAUGGGCUG<br>(65) | 52 |
| [Z]-CUUGG-[X]-[Y]-[X']-AG-[Z']<br>(hsa-miR-6886) | 66, 67 | CCUGGCGCUGA<br>(68) | 52 |
| [Z]-CUCGGGAGGGCGGG-[X]-[Y]-[X']-CCCCCCAACCCCCC-[Z']<br>(hsa-miR-615) | 69, 70 | UCGAGGGUGCUUAUUGUUCGG<br>(71) | 52 |
| [Z]-GACCUAGGCUAGG-[X]-[Y]-[X']-AGACUAGGA-[Z']<br>(hsa-miR-2116) | 72, 73 | UCCCAUGCUAAGAAGU<br>(74) | 47 |
| [Z]-GGGAAGGGC-[X]-[Y]-[X']-UUUCCC-[Z']<br>(hsa-miR-3157) | 75, 76 | GCUUUGUGCCAACACUGGGGUGAUGA<br>(77) | 47 |
| [Z]-AUCUGAGUUGGGA-[X]-[Y]-[X']-UCCCAACUCGGCCUCUGCCAUCAUU-[Z']<br>(hsa-miR-642a) | 78, 79 | GGGUGGGGAUCA<br>(80) | 47 |
| [Z]-GCAUCCUCAGGACCUGGGCUUGGGUG-[X]-[Y]-[X']-CACCCCAGCCAAUUGUCAUAGGAGC-[Z']<br>(hsa-miR-766) | 81, 82 | UCAUUUUGGAUUUG<br>(83) | 42 |

An EV-directing pre-miRNA cassette may include a sequence as shown in Table 3, or a variant sequence where the [A] and [B] sequences each include up to 5 different nucleotides to maintain the originating pri-miR's secondary structure. Although the nucleotide sequences refer to [Z] and [Z'], these are optional and may not be present. The fold increase reflects a measured increase in mature miRNA encoded by the wild-type pre-miRNA sequence in EVs derived from tumor cells infected by Vaccinia virus.

TABLE 3

Cellular miRNAs enriched more than 40-fold in EVs after Vaccinia virus infection.

| Nucleotide sequence (name of originating miR stem-loop sequence) | SEQ ID Nos for [A],[B] | Exemplary loop sequence (SEQ ID NO) | fold increase in EVs observed |
|---|---|---|---|
| [Z]-AGCCUCG-[X]-[Y]-[X']-CUUUUUUGGCG (hsa-miR-484) | 84, 85 | AAACCCUAA AUAGGGACUUU (86) | 141 |
| [Z]-CGGAAAAUUUGCCAAGGGUUUGGG-[X]-[Y]-[X']-CCUGAGGCCUGGAAUUGCCAUCCU-[Z'] (hsa-miR-181c) | 87, 88 | UUGGGCAGCU CAGGCA (89) | 129 |
| [Z]-CUCCCCAUGGCC-[X]-[Y]-[X']-GGACCUGGGGAC-[Z'] (hsa-miR-150) | 27, 28 | CUGGGCUCAG ACC (29) | 116 |
| [Z]-CCAGAGGUUGUAACGUUGUCUAUAU-[X]-[Y]-[X']-AUAUGGUCGAUGCAAAAACUUCA-[Z'] (hsa-miR-10b) | 90, 91 | UGGUAUCCGU AUAGUC (92) | 64 |
| [Z]-GCC-[X]-[Y]-[X']-GGC-[Z'] (hsa-miR-199a1) | 93, 94 | AGGAGGCUCU CAAUGUGU (95) | 62 |
| [Z]-UACCGACCCUCGAUUUGGU-[X]-[Y]-[X']-ACAAUGUCCUCAUGG-[Z'] (hsa-miR-659) | 96, 97 | AGAGUCACAG UCUCUUC (98) | 50 |
| [Z]-CCU-[X]-[Y]-[X']-AG-[Z'] (hsa-miR-6511a) | 99, 100 | GCAGAGGGUU GCGCCC (101) | 50 |
| [Z]-UACUU-[X]-[Y]-[X']-GAGUA-[Z'] (hsa-miR-381) | 102, 103 | UCGGUUUAUU GACAUGGAA (104) | 46 |
| [Z]-CCUUAGCAGAGC-[X]-[Y]-[X']-GCUACUGCUAGGC-[Z'] (hsa-miR-122) | 105, 106 | UGUCUAAACU AUCA (107) | 46 |
| [Z]-CUGUGUGUGAUGAGC-[X]-[Y]-[X']-UCUUAUUGCAUAUACA-[Z'] (hsa-miR-449a) | 108, 109 | UGAAUAUGUG AAUGGC (110) | 46 |

An EV-directing pre-miRNA cassette may include a sequence as shown in Table 4, or a variant sequence where the [A] and [B] sequences each include up to 5 different nucleotides to maintain the originating pri-miR's secondary structure. Although the nucleotide sequences refer to [Z] and [Z'], these are optional and may not be present. The fold increase reflects a measured increase in mature miRNA encoded by the wild-type pre-miRNA sequence derived from tumor cells infected by herpes simplex virus type 1 (HSV-1).

TABLE 4

Cellular miRNAs enriched more than 40-fold in EVs after HSV-1 infection.

| Nucleotide sequence (name of originating miR stem-loop sequence) | SEQ ID Nos for [A], [B] | Exemplary loop sequence (SEQ ID NO) | fold increase in EVs observed |
|---|---|---|---|
| [Z]-GCC-[X]-[Y]-[X']-GGC-[Z'] (hsa-miR-199a1) | 93, 94 | AGGAGGCUCU CAAUGUGU (95) | 252 |
| [Z]-UGUCCCCCCGGC-[X]-[Y]-[X']-GCCCGGAAGGACC-[Z'] (hsa-miR-152) | 111, 112 | CGGGCUCUGG AGCAG (113) | 66 |
| [Z]-CCCAUUGGCA-[X]-[Y]-[X']-UGUCAGUGUG-[Z'] (hsa-miR-99a) | 23, 24 | GUGAAGUGGA CCGCA (25) | 58 |
| [Z]-GUACUUGG-[X]-[Y]-[X']-CCAAGAGC-[Z'] (hsa-miR-3129) | 114, 115 | GCCUGUUAAU GAAUUC (116) | 47 |
| [Z]-GGAGAG-[X]-[Y]-[X']-CUUUCC-[Z'] (hsa-miR-31) | 117, 118 | GUUGAACUGG GAACC (119) | 44 |
| [Z]-AACACAGUGGG-[X]-[Y]-[X']-CCCACUCUGUG-[Z'] (hsa-miR-95) | 120, 121 | GAAAUGCGUU ACA (122) | 44 |
| [Z]-GGCUACAGUCUUUCUUCAUGUGACUCGUGG-[X]-[Y]-[X']-UCAAUUGUCAUCACUGGC-[Z'] (hsa-miR-204) | 123, 124 | GAGAAUAUAU GAAGGAG (125) | 40 |
| [Z]-UGGGGGAGUGAAGAG-[X]-[Y]-[X']-CUCUUCAUUUCCCCAUAUCUACUUAC-[Z'] (hsa-miR-577) | 126, 127 | AUGAAUCUGA GGC (128) | 40 |
| [Z]-UCAUGCUGUGG-[X]-[Y]-[X']-UUACGGUUUGA-[Z'] (hsa-miR-518b) | 129, 130 | UUGUCUGAAA GAAAA (131) | 40 |

An EV-directing pre-miRNA cassette may include a sequence as shown in Table 5, or a variant sequence where the [A] and [B] sequences each include up to 5 different nucleotides to maintain the originating pri-miR's secondary structure. Although the nucleotide sequences refer to [Z] and [Z'], these are optional and may not be present. The fold increase reflects a measured increase in mature miRNA encoded by the wild-type pre-miRNA sequence derived from herpes simplex virus type 1 (HSV-1).

TABLE 5

Viral miRNAs enriched more than 2-fold in EVs after HSV-1 infection.

| Nucleotide sequence (name of originating miR stem-loop sequence) | SEQ ID Nos for [A], [B] | Exemplary loop sequence (SEQ ID NO) | fold increase in EVs observed |
|---|---|---|---|
| [Z]-GCGCUC-[X]-[Y]-[X']-GGGCGC-[Z'] (hsv1-miR-H5-3p) | 132, 133 | CUCAGUGCCGC CAAUCUCAG (134) | 2752.35 |
| [Z]-GGCCCACUCGCACG-[X]-[Y]-[X']-UGCGCCGGCC-[Z'] (hsv1-miR-H17-3p) | 135, 136 | UGGGCGCGCCG CUGCGGCCCGU GUACG (137) | 12.4661 |
| [Z]-GCGCAGAGAGCCUCGUUAAGAG-[X]-[Y]-[X']-CUGCUGCCGGGGACUCUUCGC-[Z'] (hsv1-miR-H16-5p) | 138, 139 | CACAUACGC (140) | 7.20522 |

TABLE 5-continued

Viral miRNAs enriched more than 2-fold in EVs after HSV-1 infection.

| Nucleotide sequence (name of originating miR stem-loop sequence) | SEQ ID Nos for [A], [B] | Exemplary loop sequence (SEQ ID NO) | fold increase in EVs observed |
|---|---|---|---|
| [Z]-CGGGGGGCCGG-[X]-[Y]-[X']-CCGUUCCCCUCG-[Z'] (hsv1-miR-H6-5p) | 141, 142 | GGAUGGGUAUC AGGACUUC (143) | 5.70939 |
| [Z]-CGAGGGGAACGG-[X]-[Y]-[X']-CCGGCCCCCCG-[Z'] (hsv1-miR-H1-3p) | 144, 145 | AGUCCUGAUAC CCAUCC (146) | 5.61135 |
| [Z]-GGAGUCGGGCACGGCGC-[X]-[Y]-[X']-CGCGUUCUCACUUC-[Z'] (hsv1-miR-H12) | 147, 148 | UAAUAUAUAUA UA (149) | 4.4152 |
| [Z]-GAAGAGGGG-[X]-[Y]-[X']-UUCCCUCUUCUC-[Z'] (hsv1-miR-H7-3p) | 150, 151 | UGGUCUGGGUC CGUCC (152) | 2.49986 |
| [Z]-GCG-[X]-[Y]-[X']-CGC-[Z'] (hsv1-miR-H13) | 153, 154 | UAUAUAUAUAU UA (155) | 2.35285 |

In some examples, the present disclosure provides a virus whose genome includes a nucleotide sequence that encodes an EV-directing pre-miRNA or an EV-directing pri-miRNA. In one example, the virus is a vesicular stomatitis virus, or variant thereof, whose genome includes a nucleotide sequence that encodes a pre-miRNA or pri-miRNA cassette whose sequence includes: stem structure sequence SEQ ID NO: 20, sense miRNA sequence [X], loop sequence SEQ ID NO: 22, anti-sense miRNA sequence [X'], and stem structure sequence SEQ ID NO: 21. The VSV variant may be VSVΔ51, or VSV pseudotyped with LCMV's G protein. In another example, the virus is a vaccinia virus, or variant thereof, whose genome includes a nucleotide sequence that encodes a pre-miRNA or a pri-miRNA cassette whose sequence includes: stem structure sequence SEQ ID NO: 84, sense miRNA sequence [X], loop sequence SEQ ID NO: 86, anti-sense miRNA sequence [X'], and stem structure sequence SEQ ID NO: 85. In yet another example, the virus is a herpes simplex virus type 1 (HSV-1), or variant thereof, whose genome includes a nucleotide sequence that encodes a pre-miRNA or a pri-miRNA cassette whose sequences includes: stem structure sequence SEQ ID NO: 93, sense miRNA sequence [X], loop sequence SEQ ID NO: 95, anti-sense miRNA sequence [X'], and stem structure sequence SEQ ID NO: 94. As discussed above, the [X] and [X'] sequences may be replaced with sequences that form a therapy-enhancing miRNA hairpin according to the present disclosure. For example, the [X] and [X'] sequences may be replaced with any one of the pairs of sequences shown in Table 1.

A cassette encoding a miRNA hairpin may be inserted into a virus, resulting in a virus whose genome includes the cassette. The nucleotide sequence of the cassette may be prepared by selecting stem structure sequences [A] and [B] according to Table 2, Table 3, Table 4, Table 5, a loop sequence [Y], sense and anti-sense sequences [X] and [X'], and optionally flanking sequences [Z] and [Z']. Nucleotide sequences corresponding to one or more restriction enzyme cleavage sites may be added at each end of the cassette for cloning purposes. As discussed above, it may be beneficial to select sequences that mimic the paired/unpaired relationship of nucleotides in the originating miR stem-loop sequence. Mimicking the paired/unpaired relationship may result in a pre-miRNA or pri-miRNA having a secondary structure that better directs the miRNA hairpin to the EV. A cassette may be cloned into a viral genome using standard techniques.

For example, a homologous recombination approach may be used to generate new recombinant vaccinia viruses expressing a cassette encoding the desired miRNA hairpin. In such an example, Hela cells are transfected using Lipofectamine 2000 with PCR products that contain a cassette sequence, a fluorescent protein marker, and around 400 bp of flanking sequences that overlap with the desired vaccinia virus genome region where the cassette is to be inserted. After 4 hours of transfection, the cells are infected with wild-type vaccinia virus. Cells and supernatant are collected after 48 h and are frozen and thawed 3 times. The sample is then serially diluted and a plaque assay on U2OS cells is conducted. Single plaques that express the fluorescent protein marker are considered new recombinants and are picked using an EVOS microscope and then expanded in U2OS cells. Serial rounds of plaque purification are conducted until all plaques are fluorescent. Once the new recombinant virus is pure, the insertion of the cassette sequence is verified using any DNA or RNA sequencing method or device, such as Sanger sequencing.

In another example, VSV recombinant backbones that express miRNA hairpin sequences may be generated by purchasing or producing complementary synthetic oligonucleotides. In such an example, the complementary oligonucleotide sequences are annealed and digested using restriction enzymes. At the same time, a plasmid encoding the full cDNA sequence for the VSV virus is also digested with the same restriction enzymes and then gel purified. Annealed and digested oligonucleotides and plasmid are then ligated and the ligated product is used to transform competent E. coli strain HB101 bacteria. After identifying positive colonies by colony PCR using specific primers for the inserted cassette, the recombinant plasmid may be confirmed by DNA sequencing, such as Sanger sequencing. Then, new recombinant VSV viruses are rescued and grown as previously described in the literature, for example as disclosed by Lawson et al. in Proc Natl Acad Sci USA (1995) 92(10):4477-81, or by Ilkow et al. in Nature Medicine (2015) May; 21(5):530-6.

EV-directing pre-miRNA for a virus of interest may be identified by infecting cells with the virus of interest, isolating EVs secreted from the infected cells, and quantifying the extracellular vesicles versus cellular levels of identified miRNA species. The miRNA species may be identified and quantified by RNA sequencing or qPCR analysis. The cells may be cancer cells, such as pancreas carcinoma cells, e.g. MiaPaCa-2 cells.

Experiments

Identification of Therapy-Enhancing miRNA Hairpins

Approximately 16,000 artificial miRNAs (amiRNAs or amiRs) were inserted in cassettes based on miR30b according to the protocol outlined in Cheng et al. Cold Spring Harbor Protocols (2013), doi10.1101/pdb.prot075835. Then, these cassettes were cloned into a replicating Sindbis virus backbone thus generating a replicating Sindbis virus library encoding the amiRNAs. This library was screened by serial passaging, in cancer cell tissue culture and in mice bearing tumours. The authors of the present disclosure rationalized that miRNAs that enhanced Sindbis virus replication would result in an increase in relative frequency of the encoding Sindbis virus. The viral RNA was isolated from the enriched cells or tumor samples from the animal model, reverse transcribed into cDNA, and identified using a MiSeq sequencing system. This is generally illustrated in FIG. 2.

The MiSeq sequencing data was used to generate observed counts for each RNA species in the three replicates. Artificial miRNAs with statistically significant enrichment in the target cell types cells compared to baseline levels in the unpassaged library were identified and prioritized by one-sided t-tests. P-values were corrected for multiple comparisons by the Benjamin-Hochberg false discovery rate approach, as appropriate. The top eight candidates, sequences outlined in Table 1, were identified by fold change increase compared to the original (input) library. The results are shown in Table 6 below.

Vaccinia Virus (W) and Vesicular Stomatitis Virus (VSV) Encoding Therapy-Enhancing miRNA Hairpins FIG. 3 illustrates the genomic backbone of a VSV that includes a nucleotide sequence encoding the sense and anti-sense sequences of a miRNA hairpin. With regard to nomenclature, such a VSV may be referred to as "VSV-[name of mature miRNA]". For example, "VSV-amiR1" refers to a VSV that includes a nucleotide sequence that encodes a pre-miRNA or pri-miRNA cassette including a miRNA hairpin with stem sense and anti-sense sequences [X] and [X'] corresponding to SEQ ID NOs: 1 and 2, respectively. A control VSV was generated expressing a miRNA sequence against the green fluorescent protein (GFP). The control is referred to as "VSV-miR-GFP". Similar nomenclature is used for W.

The VSV and VV were generated by cloning a cassette into the VSV or VV backbones using the techniques discussed above.

Enhanced Cytotoxicity of VSV Encoding Therapy-Enhancing miRNA Hairpins

A human renal cell adenocarcinoma (786-0 cells) cell line, a human ovarian cancer (SKOV3 cells) cell line, or a mouse pancreatic cancer cell line (Panc02) was infected at the multiplicity of infections (MOI) of 1 with VSV-amiR-GFP (non-targeting control) or VSV-encoding amiRNA sequences shown in Table 1 ("VSV-amiR[#]").

Cell viability was measured 24, 48 and 72 hours post-infection by Alamar Blue Assay®. The results show that: in 786-0 cells, amiR6 and amiR1 enhance VSV-induced cytotoxicity (as observed at 72 h post-infection) as shown in Table 7; in SKOV3 cells: amiR6, amiR5 and amiR1 enhance VSV-induced cytotoxicity (as observed at 24 and 48 h post-infection) as shown in Table 8; and in Panc02 cells: miR1, miR2, miR3, miR6, miR8, miR9 and miR10 enhance VSV-induced cytotoxicity (as observed at 72 h post-infection) as shown in Table 9.

TABLE 6

Fold increase of amiRs in the indicated models.

| | GM38 cells | PanFib cells | MiaPaCa-2 cells | Panc02 cells | MiaPaCa-2 tumors | MiaPaCa-2 and PanFib tumors | Average of enrichment in all models tested |
|---|---|---|---|---|---|---|---|
| amiR1 | 30.24 | 66.96 | 433.75 | 433.75 | 23.86 | 1.85 | 165.07 |
| amiR2 | 0 | 2326.18 | 2328.30 | 1560.52 | 23.72 | 171.75 | 1068.41 |
| amiR3 | 39.78 | 16.87 | 14.77 | 2.29 | 0 | 62.26 | 22.66 |
| amiR5 | 0 | 12.82 | 7.02 | 12.12 | 26.85 | 28.16 | 14.49 |
| amiR6 | 13.84 | 0 | 54.96 | 5.05 | 0 | 0 | 12.31 |
| amiR8 | 0 | 4.35 | 2.49 | 4.07 | 0 | 0 | 2.18 |
| amiR9 | 0 | 1.59 | 0 | 5.85 | 30.53 | 6.38 | 7.39 |
| amiR10 | 0 | 0 | 0 | 2.2 | 110.75 | 26.52 | 23.24 |

TABLE 7

Cell viability of VSV-amiR[#] infected 786-0 cells as percent of mock treated cells.

| Time (h) | miR-GFP | amiR1 | amiR2 | amiR3 | amiR5 | amiR6 | amiR8 | amiR9 | amiR10 |
|---|---|---|---|---|---|---|---|---|---|
| 24 | 82.64 | 77.72 | 82.78 | 80.93 | 82.01 | 69.76 | 79.14 | 80.45 | 79.70 |
| 48 | 82.54 | 59.56 | 71.46 | 71.06 | 76.01 | 34.26 | 63.13 | 63.14 | 73.83 |
| 72 | 88.33 | 63.74 | 79.96 | 79.96 | 82.72 | 41.78 | 73.26 | 80.91 | 83.69 |

TABLE 8

Cell viability of VSV-amiR[#] infected SKOV3 cells as percent of mock treated cells.

| Time (h) | miR-GFP | amiR1 | amiR2 | amiR3 | amiR5 | amiR6 | amiR8 | amiR9 | amiR10 |
|---|---|---|---|---|---|---|---|---|---|
| 24 | 56.43 | 35.94 | 55.29 | 52.09 | 21.85 | 35.76 | 48.57 | 58.73 | 53.88 |
| 48 | 28.54 | 14.77 | 22.83 | 21.44 | 9.83 | 15.18 | 20.39 | 24.83 | 22.38 |
| 72 | 11.30 | 8.98 | 12.62 | 11.92 | 10.54 | 9.03 | 12.02 | 12.09 | 11.05 |

TABLE 9

Cell viability of VSV-amiR[#] infected Panc02 cells as percent of mock treated cells.

| Time (h) | miR-GFP | amiR1 | amiR2 | amiR3 | amiR5 | amiR6 | amiR8 | amiR9 | amiR10 |
|---|---|---|---|---|---|---|---|---|---|
| 24 | 89.57 | 78.47 | 86.58 | 79.49 | 79.79 | 79.80 | 77.97 | 82.72 | 80.69 |
| 48 | 63.12 | 49.83 | 65.19 | 64.29 | 66.51 | 62.37 | 51.47 | 56.91 | 65.29 |
| 72 | 78.97 | 28.56 | 50.16 | 38.48 | 70.50 | 40.24 | 29.54 | 44.74 | 40.10 |

Enhanced Virus Growth in Human Pancreatic Cancer Cell Lines or in Tumor Cores Derived from a Pancreatic Cancer Patient Tumor Two human pancreatic cancer cell lines (MiaPaCa-2, and PanC1) and a mouse pancreatic (Panc02) cell line were infected with the indicated VSV viruses at a MOI of 0.1 for 48 hours. Then, the supernatants from virally infected cells were collected and infectious virus particle production (virus titers) was quantified by plaque assay as previously described in Ilkow et al. Nat Med. (2015) 21(5):530-6. The viral titers for each VSV-amiR[#] is expressed as fold change compared to virus control (VSV-amiR-GFP). The results are illustrated in the following table.

TABLE 10

Fold increase in virus titer relative to VSV-amiR-GFP. Note that VSV-amiR-GFP titers were arbitrarily set at 1.

| Cell line | miR-GFP | amiR1 | amiR2 | amiR3 | amiR5 | amiR6 | amiR8 | amiR9 | amiR10 |
|---|---|---|---|---|---|---|---|---|---|
| MiaPaCa-2 | 1 | 2.97 | 15.86 | 17.24 | 6.69 | 66.21 | 15.86 | 16.55 | 19.31 |
| PanC1 | 1 | 0.805 | 1.8 | 2.24 | 1.37 | 3.66 | 1.63 | 2.07 | 2.71 |
| PanC02 | 1 | 1.48 | 1.67 | 4.38 | 0.5 | 1.38 | 10.63 | 10.21 | 5.00 |

Tumor cores (approximately 2 mm by 2 mm) derived from a pancreatic cancer patient (P006) were infected with 1E4 pfu (plaque forming units) of VSV-amiR control or VSV-amiR[#] for 48 hours and then infectious virus particles were quantified by plaque assay. Virus titers are expressed as pfu (plaque-forming units) per milliliter (ml). ±SD among replicates (n=6 tumor cores per virus construct) is indicated.

TABLE 11

Virus titers in pfu/mL.

| | miR-GFP | amiR1 | amiR2 | amiR3 | amiR5 | amiR6 | amiR8 | amiR9 | amiR10 |
|---|---|---|---|---|---|---|---|---|---|
| Virus titer | 9130 ± 2820 | 13900 ± 6490 | 19100 ± 4320 | 39100 ± 15800 | 7300 ± 2980 | 94000 ± 35000 | 60700 ± 11800 | 53800 ± 16200 | 9600 ± 2840 |

The results show that:

in MiaPaCa-2 cells: amiR2, amiR3, amiR6, amiR8, amiR9 and amiR10 enhanced VSV replication or growth;

in PanC1 cells: amiR6, and at a less extend amiR3, amiR9 and amiR10 enhanced VSV replication;

in Panc02 cells: amiR3, amiR6, amiR8, amiR9, and amiR10 enhanced VSV replication; and in tumor cores derived from Patient-6: amiR3, amiR6, amiR8, and amiR9 enhanced VSV replication.

VSV-miR-GFP (control) or VSV-amiR6 were delivered intravenously (IV) into mice bearing subcutaneously implanted HPAF II tumors (human Pancreatic cancer model). After 72 hours, tumors were collected, homogenized and titered by plaque assay (n=8 per group). The mean virus titres (pfu/mg) were: 3,912 for VSV-miR-GFP, and 35,152.6 for VSV-amiR6 (n=4 animals/tumors per group).

VSV-amiR6 Shows Enhanced Cytotoxicity in Cancer Cells, in Tumors In Vivo, and in Ex Vivo Patient-Derived Tumor Samples As discussed above, a VSV encoding a cassette containing a sense and anti-sense stem sequence according to SEQ ID NOs: 9 and 10 is referred to as "VSV-amiR6". In the experimental results discussed herein, the VSV-amiR6 specifically includes a sequence according to SEQ ID NO: 181.

VSV-amiR6 shows enhanced cytotoxicity in 786-0 cells (a human kidney cancer cell line). 786-0 cells were infected with a VSV virus control or with VSV-amiR6 at three different MOIs (0.01, 0.1, and 1). After 24 or 48 hours post-infection (hpi), cells were stained with crystal violet to label live cells and absorbance was quantified using a spectrometer. All MOIs were tested using VSV-amiR6 or a control VSV virus expressing the enhance Green Fluorescent protein (eGFP) as illustrated in Table 12. Values are expressed as a proportion of control (mock infected 786-0 cells at 24 or 48 hours, respectively).

TABLE 12

Cell viability of 786-0 infected cells at indicated time points and MOIs.

|  | VSV-eGFP | | VSV-amiR6 | |
| --- | --- | --- | --- | --- |
|  | 24 hpi | 48 hpi | 24 hpi | 48 hpi |
| MOI = 0.01 | 1.15 | 0.83 | 1.19 | 0.16 |
| MOI = 0.1 | 1.03 | 0.69 | 0.79 | 0.055 |
| MOI = 1 | 0.99 | 0.53 | 0.46 | 0.022 |

Panc02 and PanC1 (mouse and human pancreatic cancer cell lines, respectively) were mock-infected or infected with VSV control or VSV-amiR6 at an MOI of 0.1 for 48 hours.

Seven different cancer cell lines (HPAC, MiaPaca, PanC1, 786-0, HPAF II, BxPC3, Panc02), pancreatic cancer-associated fibroblasts (PCa-CAF) and normal fibroblasts (GM38) were infected with VSV-amiR6 or VSV-miR-GFP (control virus) at a multiplicity of infection of 1. After 48 hours, cell viability among biological replicates (n=6 per group) was measured by Alamar Blue Assays®. amiR6 did not enhance VSV killing in healthy fibroblasts (GM38) but enhanced killing in all cancer cells lines and cancer associated fibroblasts (PCa-CAF). The results are illustrated below:

TABLE 13

Cell viability indicated as percent of control (relative to mock infected cells).

|  | HPAC | MiaPaca | PanC1 | 786-O | HPAF II | BxPC3 | PanCO2 | PCa-CAF | GM38 |
| --- | --- | --- | --- | --- | --- | --- | --- | --- | --- |
| VSV-amiR6 | 53.83 | 38.99 | 37.53 | 34.26 | 58.73 | 55.17 | 40.24 | 49.63 | 84.38 |
| VSV-amiR-GFP | 77.42 | 50.14 | 46.55 | 82.54 | 72.73 | 84.45 | 78.97 | 87.82 | 85.72 |

PBS (vehicle control), VSV-miR-GFP (control), or VSV-amiR6 (1E8 pfu/mouse) was delivered intratumorally (IT) into mice bearing subcutaneously implanted HPAF II tumors (human Pancreatic cancer model) when the tumors all reached an approximate size of 5×5 mm (day 29 post-tumor implantation). After 59 days post-tumor implantation, tumor volume was measured using calipers. Tumor volumes ($mm^3$) were: 1063.78 for PBS, 636.92 for VSV control, and 277.59 for VSV-amiR6 (average for 4 animals per group).

VSV-miR-NTC (control) or VSV-amiR6 (1E8 pfu/mouse) was delivered intraperitoneally (IP) into C57/BL6 mice bearing orthotopic pancreatic tumors (Panc02 model). After 2 weeks of virus treatment, tumor volumes were measure by magnetic resonance imaging (MRI) and tumor volumes plotted. The final tumor volumes ($cm^3$) were: 0.58 for PBS treatment; 0.54 for VSV-miR-GFP, and 0.29 for VSV-amiR6.

Figure 4:
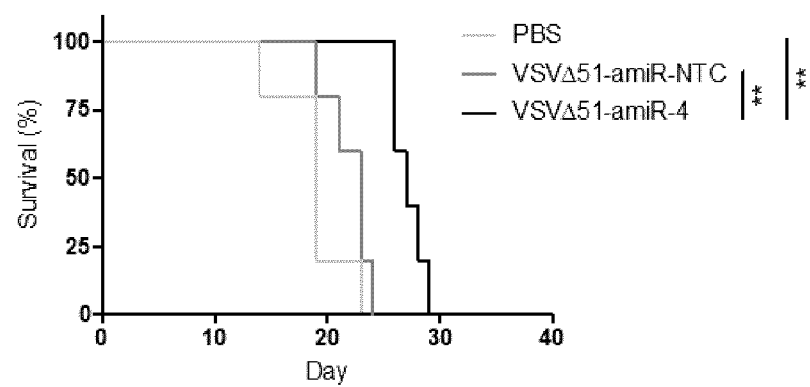

VSV-miR-NTC (control) or VSV-amiR6 was delivered intraperitoneally (IP) into C57/BL6 mice bearing orthotopic pancreatic tumors (TH04 model). Animals were then left until they reached end-point. Kaplan-Meier survival curves for mortality is shown in FIG. 4. Animals treated with VSV-amiR6 show significant improvement in survival compared to controls.

Tumor cores (approximately 2 mm by 2 mm) derived from three pancreatic cancer patients were infected with 1E4 pfu (plaque-forming units) of VSV-amiR control or VSV-amiR6 for 48 hours and then infectious virus particles were quantified by plaque assay. The mean values for virus titres are illustrated below:

TABLE 14

Virus titer (pfu/mL) 48 h after infection of pancreatic cancer derived-primary cell cultures with the indicated VSV-amiR.

|  | Patient 6 | Patient 14 | Patient 21 | Patient 25 |
| --- | --- | --- | --- | --- |
| VSV-amiR6 | 94000 | 1096.67 | 4116.67 | 577000 |
| VSV-amiR-GFP | 9130 | 119.09 | 2490.00 | 316000 |

Therapy-Enhancing miRNAs are Secreted Via Extracellular-Vesicles

Figure 5:
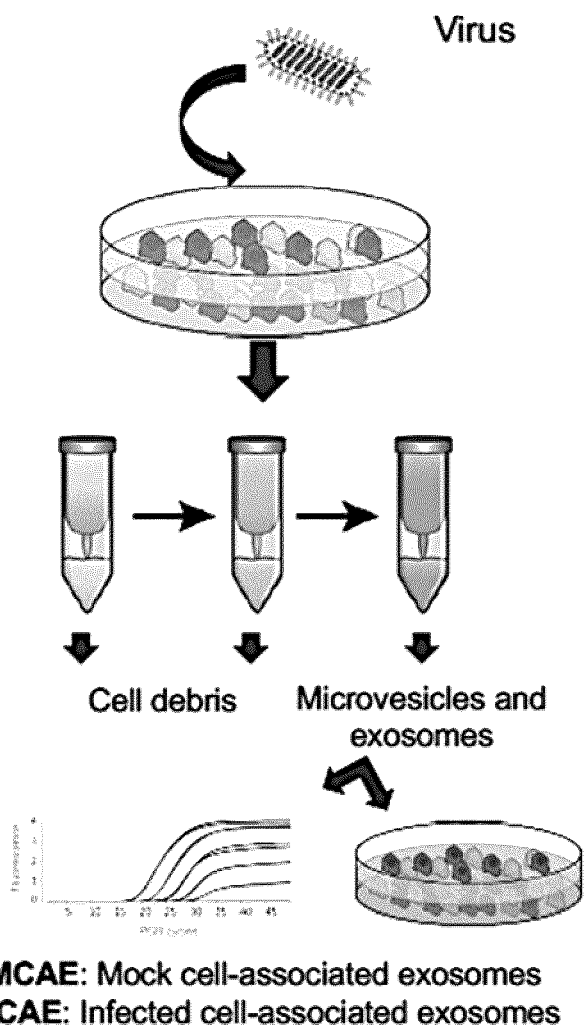

FIG. 5 illustrates the strategy used to demonstrate that therapy-enhancing miRNA according to the present disclosure are expressed and loaded in EVs budded from a virus-infected tumor cell.

Briefly, cancer cells were mock treated or infected with VSV-amiR6 at a MOI=0.1 and after 48 hours post-infection, supernatants from these samples were collected. The EVs produced and secreted were isolated from the supernatants by a differential centrifugation protocol. Total RNA purified from isolated EVs was extracted using TRIzol® and reverse transcribed to cDNA. Quantification of specific miRNAs in EVs was performed by qPCR analysis using specific primers.

Quantification of amiR6 by qPCR analysis in purified EVs was derived from mock infected HPAF II cells (Mock cell-associated EVs, MCAE) or VSV-amiR6 infected cells (Infected cell-associated EVs, ICAE). The amount of extracellular vesicular amiR6 is indicated as relative to the amount of mock infected cells extracellular vesicular hsa-let-7a (which was arbitrarily set at 1.0), a common extracellular vesicular microRNA. The results are illustrated below:

TABLE 15 miR level (relative to MCAE hsa-let-7a).

|      | hsa-let-7a | amiR6 |
|------|------------|-------|
| MCAE | 1.0        | None detected |
| ICAE | 0.86       | 1785.83 |

EV Transfer of amiR6 to Uninfected Cancer Cells Sensitizes the Uninfected Cancer Cells to GSK126

The authors of the present disclosure found that amiR6 targets and downregulates the expression of the AT-rich interactive domain-containing protein 1A (ARID1A), among other cellular messenger RNAs (mRNAs). Since it is known that pharmacological inhibition of EZH2 by GSK126 represents an anti-cancer treatment strategy when ARID1A is downregulated, the present authors tested and confirmed that EVs produced by VSV-amiR6 infected cancer cells could sensitize uninfected cancer cells to the killing activity of GSK126. This demonstrates that amiR6 increases or enhances the therapeutic effectiveness of VSV and GSK126.

qPCR analysis was used to identify cellular targets of amiR6. The fold change of mRNA levels for six different genes is shown below. Analysis of qPCR data was performed using the delta-delta Cycle Threshold (ΔΔCT method).

TABLE 16

Fold change in mRNA levels for MiaPaca-2 cells infected with VSV-amiR6 normalized to VSV-miR-GFP.

| ARID1A | BCL-9L | MED16 | PLEC | MLYCD | HDAC4 |
|--------|--------|-------|------|-------|-------|
| 0.418  | 0.496  | 0.513 | 0.572 | 0.611 | 0.741 |

The downregulation in expression of ARID1A in infected cells was confirmed by Western blot analysis, with PanC1 cell cells having a 90% reduction in ARID1A expression compared to controls at 24 hours (data not shown).

Human pancreatic (HPAFII, BXPC3, and PanC1), human kidney cancer (786-0), or mouse breast carcinoma (4T1) cell line cultures, or a patient-derived pancreatic cancer cell line (Patient 25), were tested. The cells were mock-infected, or infected with VSV-amiR6 or VSV control at MOI=1. After 18 hours, the cells were then treated with GSK126 (10 μM). After 72 h, the VSV-amiR6/GSK126 treated cells were more affected by the GSK126 cytotoxicity than control cells. Cytotoxicity was measured in the BXPC3, Patient 25, 4T1, and 786-0 samples by staining live cells with crystal violet stain, lifting the stain and quantifying absorbance at 570 nm using a spectrophotometer. In the case of HPAF II, cell viability was quantified using the Alamar Blue® assay. Cell viability of mock treated cells was set at 100%. Cell viability (%) of all experimental samples is expressed relative to their corresponding mock vehicle-treated cells. The results are illustrated in the table below:

TABLE 17

GSK126-induced cytotoxicity (%) in mock or VSV-miRNA treated cells.

| | DMSO (vehicle control) | | | GSK126 | | |
|---|---|---|---|---|---|---|
| | Mock | VSV-miR-GFP | VSV-amiR6 | Mock | VSV-miR-GFP | VSV-amiR6 |
| HPAF II | 100 | 71.77 | 66.72 | 90.19 | 70.01 | 35.76 |
| 786-0 | 100 | 90.83 | 81.95 | 111.99 | 80.81 | 32.22 |
| BXPC3 | 100 | 73.79 | 63.37 | 96.07 | 71.59 | 47.56 |
| 4T1 | 100 | 87.59 | 78.40 | 113.50 | 87.82 | 38.56 |
| Patient 25 | 100 | 73.89 | 54.03 | 80.82 | 39.04 | 10.18 |

Naïve HPAF II, 786-0 cells, Patient 25 or BXPC3 cells were also exposed to isolated EVs derived from their respective counterparts (HPAF II, 786-0, Patient 25, or BXPC3, respectively) mock-infected or infected with VSV control or VSV-amiR6, and after 24 hours were also treated with vehicle control (DMSO) or with GSK126 (10 μM). The results, illustrated below, show that the EVs derived from VSV-amiR6 infected cells induce cytotoxicity to GSK126.

TABLE 18

Cell viability per each condition is expressed as a percentage of control (cells treated with mock EVs and vehicle control). Mean values for 4 biological replicates are shown for 786-0, and for 3 biological replicates for BXPC3.

| | DMSO (vehicle control) | | | GSK126 | | |
|---|---|---|---|---|---|---|
| | EVs from Mock | EVs from VSV-miR-GFP | EVs from VSV-amiR6 | EVs from Mock | EVs from VSV-miR-GFP | EVs from VSV-amiR6 |
| HPAF II | 100 | 80.27 | 69.03 | 96.24 | 84.71 | 45.30 |
| 786-0 | 100 | 90.14 | 66.12 | 98.35 | 84.29 | 40.28 |
| BXPC3 | 100 | 85.36 | 78.42 | 90.78 | 76.66 | 58.90 |
| Patient 25 | 100 | 92.44 | 84.22 | 64.14 | 31.36 | 10.51 |

Human pancreatic (HPAFII) cells were grafted as tumours in SCID mice subcutaneously, and were tested as follows. After successful establishment of the tumours, mice were treated intratumorally with PBS (vehicle control), or with VSV-amiR6 (3 doses at 1E8 pfu/mouse). After the first virus injection, animals were treated daily for 10 consecutive days with GSK126 (50 mg per kg mouse total weight) or vehicle control, injected intraperitoneally. Tumor size was measured using calipers, and with tumours initially being of a similar volume (5 $mm^3$), at day 56, tumor volumes were: 1609.3 $mm^3$ for PBS+GSK126, 763.2 $mm^3$ for VSV-amiR6+vehicle control, and 265.1 $mm^3$ for VSV-amiR6+GSK126 (average for 4 animals per group).

Figure 6:
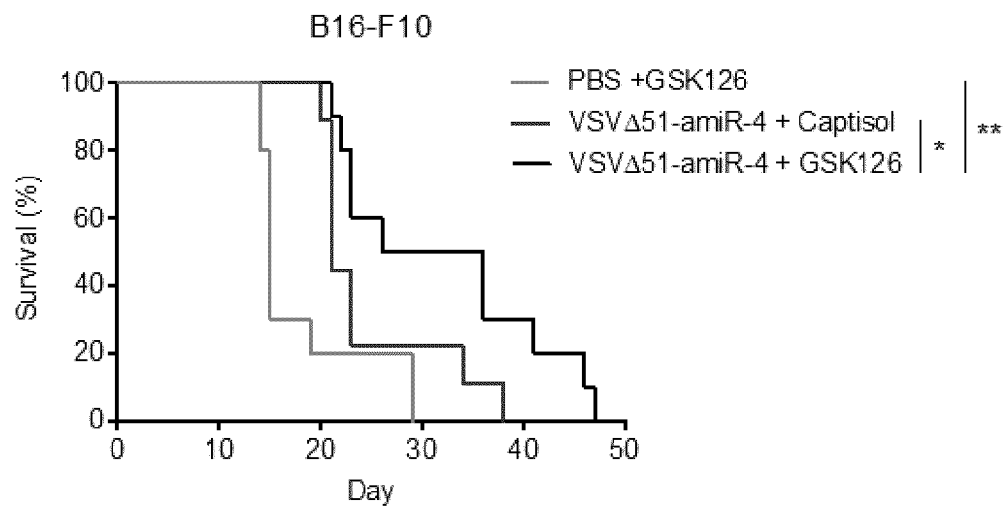

In a different tumor model, three doses (every other day) of vehicle control (PBS), VSV-miR-NTC (control) or VSV-amiR6 (1E8 pfu/mouse) were delivered intraperitoneally (IP) into C57/BL6 mice bearing intraperitoneal B16-F10 melanoma tumors. Then, mice were treated intraperitoneally with GSK126 (50 mg/kg) for 10 consecutive days. Animals were then left until they reach end point. Kaplan-Meier survival curve for mortality is shown in FIG. 6.

Identification of Extracellular Vesicle-Directing Cassettes

Figure 7:
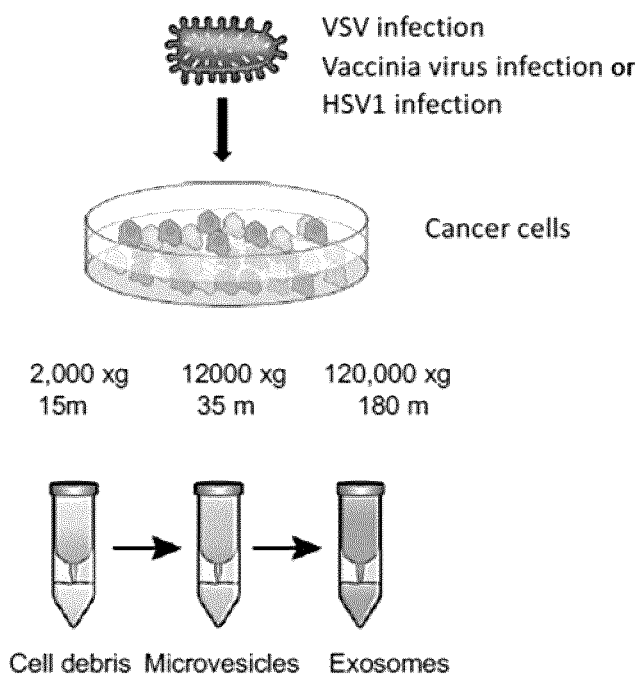

FIG. 7 illustrates the strategy used to identify miRNA sequences enriched in EVs budded from VSV-infected, Vaccinia virus-infected, and HSV-1-infected MiaPaCa-2 cancer cells.

Briefly, MiaPaCa-2 cells were mock treated or infected with (a) VSVΔ51, (b) Vaccinia virus, or (c) HSV-1, at a MOI=0.1 and after 48 hours, supernatants from these samples were collected. The EVs produced and secreted were isolated from the supernatants by a standard differential centrifugation protocol. Total RNA from the cells and their derived EVs was isolated and subjected to small RNA sequencing to identify and quantify the miRNA species enriched in EVs compared to the cells that produced them. Bioinformatic analysis was conducted to calculate fold change of extracellular vesicular versus cellular miRNA levels. The pre-miRs that resulted in more than a 40-fold enrichment of the encoded human origin miRNA hairpins are shown in Table 2 (VSV infection), Table 3 (Vaccinia virus infection), and Table 4 (HSV-1 infection), and the pre-miRs that resulted in more than double enrichment of the encoded viral miRNA hairpins are shown in Table 5 (HSV-1 infection).

Extracellular Vesicle-Directing Cassettes Express Encoded miRNA Hairpins

VSVΔ51, an oncolytic variant of VSV, encoding various miRNA hairpins were prepared. The cassettes encoding the miRNA included stem structure sequences [A] and [B], sense and antisense shRNA sequences [X] and [X'], loop sequence [Y], and optional flanking sequences [Z] and [Z'] in the order: [Z]-[A]-[X]-[Y]-[X']-[B]-[Z']. The sequences or their SEQ ID NOs are shown in Table 19, below, with the full sequence of the miR constructs provided in Appendix B. The table identifies the intended target of the shRNA sequences, and the name of the originating miR stem-loop sequence.

TABLE 19

[X] and [X'] shRNA sequences, with their respective [Y] loop sequence, and [A] and [B] sequences.

| shRNA target | [Z], [A] (SEQ ID NOs) | [X] sequence (SEQ ID NO) | [Y] sequence (SEQ ID NO) | [X'] sequence (SEQ ID NO) | B, [Z'] (SEQ ID NOs) | originating miR stem-loop sequence |
|---|---|---|---|---|---|---|
| BRCA1 (mouse/human) | 30 | CACAAAGTGTG ACCACAT (156) | ATTT (157) | ATGTGGTCACA CTTTGTG (158) | 31 | hsa-miR451 |
| BRCA2 (mouse/human) | 30 | TATCAGGATAT GCGAATTA (159) | AGAA (160) | TAATTCGCATA TCCTGTA (161) | 31 | hsa-miR451 |
| BRCA2 (human only) | 18, 39 | AACTAGTAGGA TATTGTTCTTC (162) | CTGTGAAGCC ACAGATGGG (163) | GAAGAACAATA TCCTACTAGTT (164) | 40, 19 | hsa-miR30 |
| PDL1 (mouse) | 30 | TTCAACACTGC TTACGTC (165) | TCCT (166) | GACGTAAGCAG TGTTGAA (167) | 31 | hsa-miR451 |
| Luciferase | 39 | CTGGGCGTTAA TCAAAGA (168) | CTGTGAAGCC ACAGATGGG (163) | TCTTTGATTAAC GCCCAG (169) | 40 | hsa-miR30 |
| eGFP | 39 | TCTATATCATG GCCGACA (170) | CTGTGAAGCC ACAGATGGG (163) | TGTCGGCCATG ATATAGA (171) | 40 | hsa-miR30 |
| LacZ | 39 | TGACCTATCCC ATTACGG (172) | CTGTGAAGCC ACAGATGGG (163) | CCGTAATGGGA TAGGTCA (173) | 40 | hsa-miR30 |

The [X] and [X'] shRNA sequences shown in Table 19 were modified from their respective native shRNA so that the resulting cassette mimics the native miRNA's secondary structure. The native shRNA sequences used to target human and/or mouse BRCA1, BRCA2 and PDL1 targets ("BRCA1 (h/m)", "BRCA2(h/m)", and "PDL1(m)") were trimmed (resulting in SEQ ID Nos: 156, 158, 159, 161, 165 and 167) to create a cassette mimicking the natural secondary structure of miR451.

RT-qPCR analysis was used to demonstrate the down-regulation of BRCA1 upon infection of Human osteosarcoma cells (U2OS), and human breast cancer (MCF7 and T47D) cell lines with VSVΔ51 encoding a cassette including: SEQ ID NO: 30, followed by SEQ ID NO: 156, followed by SEQ ID NO: 157, followed by SEQ ID NO: 158, and followed by SEQ ID NO 31 (referred to as "VSVΔ51-shRNA-BRCA1(h/m)"). U2OS cells were infected with VSVΔ51 virus control or with VSVΔ51-shRNA-BRCA1(h/m) at an MOI of 0.01. MCF7 and T47D cells were infected at a MOI of 0.1. RNA from infected cells was harvested after 48 h post-infection and processed for RT-qPCR using specific primers for BRCA1. Analysis of qPCR data was performed using the ΔΔCT method. The levels of BRCA1 for cells infected with the VSVΔ51 were set at 1.

TABLE 20 qPCR for cells infected with VSVΔ51 targeting human and mouse BRCA1.

|  | VSVΔ51 control | VSVΔ51-shRNA-BRCA1(h/m) |
|---|---|---|
| U2OS cells | 1 | 0.033 |
| MCF7 cells | 1 | 0.39 |
| T47D cells | 1 | 0.13 |

Similarly, RT-qPCR analysis was used to demonstrate the downregulation of BRCA2 upon infection of Human osteosarcoma cells (U2OS), and human breast cancer (MCF7 and T47D) cell lines with VSVΔ51 encoding a cassette including: SEQ ID NO: 30, followed by SEQ ID NO: 159, followed by SEQ ID NO: 160, followed by SEQ ID NO: 161, and followed by SEQ ID NO: 31 (referred to as "VSVΔ51-shRNA-BRCA2(h/m)"). U2OS cells were infected with VSVΔ51 virus control or with VSVΔ51-shRNA-BRCA2(h/m) at an MOI of 0.01. MCF7 and T47D cells were infected at a MOI of 0.1. RNA from infected cells was harvested after 48 h post-infection and processed for RT-qPCR using specific primers for BRCA2. Analysis of qPCR data was performed using the ΔΔCT method. The levels of BRCA2 for cells infected with the VSVΔ51 were set at 1.

TABLE 21 qPCR for cells infected with VSVΔ51 targeting human and mouse BRCA2.

|  | VSVΔ51 control | VSVΔ51-shRNA-BRCA2(h/m) |
|---|---|---|
| U2OS cells | 1 | 0.17 |
| MCF7 cells | 1 | 0.59 |
| T47D cells | 1 | 0.34 |

In another experiment targeting only human BRCA2 ("BRCA(h)"), a cassette was prepared that included sequences according to: SEQ ID NO: 18, followed by SEQ ID NO: 39, followed by SEQ ID NO: 162, followed by SEQ ID NO: 163, followed by SEQ ID NO: 164, followed by SEQ ID NO: 40, and followed by SEQ ID NO: 19. A virus encoding such a cassette may be referred to herein as "[virus]-shRNA-BRCA2(h)". RT-qPCR analysis was used to demonstrate the downregulation of BRCA2 upon infection of Human osteosarcoma cells (U2OS), and human breast cancer (MCF7) cells with VSVΔ51-shRNA-BRCA2 (h). U2OS cells were infected with VSVD51 virus control or with VSVΔ51-shRNA-BRCA2(h) at an MOI of 0.01. MCF7 cells were infected at a MOI of 0.1. RNA from infected cells was harvested after 48 h post-infection and processed for RT-qPCR using specific primers for BRCA2. Analysis of qPCR data was performed using the ΔΔCT method. The levels of BRCA2 for cells infected with the VSVΔ51 were set at 1.

TABLE 22 qPCR for cells infected with VSVΔ51 targeting human BRCA2.

|  | VSVΔ51 control | VSVΔ51-shRNA-BRCA2(h) |
|---|---|---|
| U2OS cells | 1 | 0.17 |
| MCF7 cells | 1 | 0.59 |

In another experiment targeting mouse PDL1 ("PDL1 (m)"), a cassette was prepared that included sequences according to: SEQ ID NO: 30, followed by SEQ ID NO: 165, followed by SEQ ID NO: 166, followed by SEQ ID NO: 167, and followed by SEQ ID NO:31. A virus encoding such a cassette may be referred to herein as "[virus]-shRNA-PDL1(m)". Western blot analysis was used to demonstrate the downregulation of PDL1 upon infection of mouse breast cancer 4T1 cells with VSVΔ51-shRNA-PDL1(m). 4T1 cells were left untreated or infected with VSVΔ51 virus control or with VSVΔ51-shRNA-PDL1(m) at an MOI of 0.1. Total proteins from mock-treated or infected cells were harvested after 48 h post-infection and processed for Immunoblot analysis using specific antibodies for PDL1 and tubulin. Western blot data was quantified using Image J software and the levels of PDL1 in each sample normalized to tubulin (loading control). VSVΔ51-shRNA-PDL1(m) infected cells have a 47.7% reduction in PDL1 expression relative to VSVΔ51 infected cells.

Extracellular Vesicle-Directing Cassettes Express Multiple Encoded miRNA Hairpins in Tandem Three miR hairpin casettes (illustrated in Table 19) were prepared:

- a cassette that included sequences according to: SEQ ID NO: 30, followed by SEQ ID NO: 168, followed by SEQ ID NO: 163, followed by SEQ ID NO: 169, and followed by SEQ ID NO:31 (SEQ ID NOs: 168 and 169 target Fluc (Firefly luciferase));
- a cassette that included sequences according to: SEQ ID NO: 30, followed by SEQ ID NO: 170, followed by SEQ ID NO: 163, followed by SEQ ID NO: 171, and followed by SEQ ID NO:31 (SEQ ID NOs: 170 and 171 target eGFP (enhanced green fluorescence protein)); and
- a cassette that included sequences according to: SEQ ID NO: 30, followed by SEQ ID NO: 172, followed by SEQ ID NO: 163, followed by SEQ ID NO: 173, and followed by SEQ ID NO: 31 (SEQ ID NOs: 172 and 173 target LacZ (8-galactosidase)).

Figure 8:
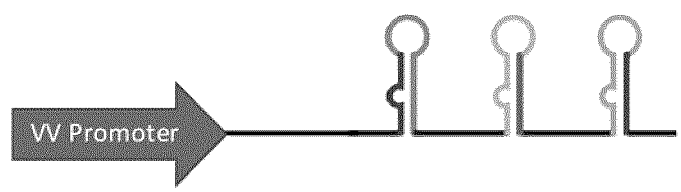
Figure 9:
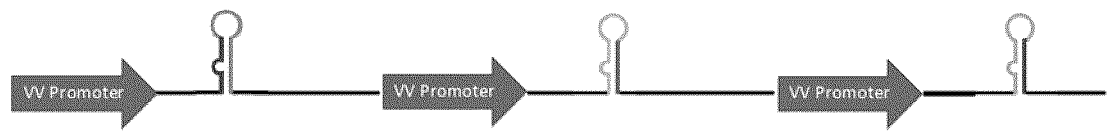

The three miR hairpin cassettes were cloned in tandem from a single viral promoter (FIG. 8) generating a single polycistronic transcript, or each of the three cassettes was cloned with its own viral promoter (FIG. 9), generating three individual constructs. These constructs were cloned in the B14R locus of a vaccinia virus backbone using the standard homologous recombination approach thus generating VVΔB14R-amiR-PolyLFG for the polycistronic construct and VVΔB14R-amiR-MonoLFG for the three individual constructs. Control vaccinia viruses were also generated with single viruses each encoding a single cassette: VVΔB14R-amiR-LacZ, VVΔB14R-amiR-Fluc, and VVΔB14R-amiR-eGFP, as well as an empty VVΔB14R virus. U2-OS (Human osteosarcoma) cells were infected with the Copenhagen strain of vaccinia-viruses at an MOI of 0.1, RNA was collected with TriZol after 24 or 48 hr post-infection and miR construct levels were quantified by qPCR using specific primers that detect the mature miR-eGFP (Table 23), miR-LacZ (Table 24), or the miR-Fluc (Table 25) sequence.

TABLE 23

Copy numbers of mature amiR-eGFP were determined by qPCR analysis using specific primers for amiR-eGFP.

|  | MOI 0.1 | | | |
|---|---|---|---|---|
|  | 24 hr | | 48 hr | |
|  | Avg Quant. | SD | Avg Quant. | SD |
| Mock | 1.145 | 0.54 | 0.75 | 0.89 |
| VVΔB14R | 2.08 | 1.31 | 1.65 | 1.02 |
| VVΔB14R-amiR-LacZ | 1.68 | 1.97 | 1.04 | 0.83 |
| VVΔB14R-amiR-Fluc | 0.92 | 1.34 | 0 | 0 |
| VVΔB14R-amiR-eGFP | 52160.07 | 4660.47 | 37318.18 | 4127.06 |
| VVΔB14R-amiR-PolyLFG | 66970.85 | 10273.33 | 28408.35 | 1988.03 |
| VVΔB14R-amiR-MonoLFG | 51565.83 | 7620.46 | 20616.33 | 2274.47 |

TABLE 24

Copy numbers of mature amiR-Fluc were determined by qPCR analysis using specific primers for amiR-Fluc.

|  | MOI 0.1 | | | |
|---|---|---|---|---|
|  | 24 hr | | 48 hr | |
|  | Avg Quant. | SD | Avg Quant. | SD |
| Mock | 0 | 0 | 0 | 0 |
| VVΔB14R | 0 | 0 | 0 | 0 |
| VVΔB14R-amiR-LacZ | 0 | 0 | 0 | 0 |
| VVΔB14R-amiR-Fluc | 25850.94 | 8182.97 | 65385.83 | 19599.70 |
| VVΔB14R-amiR-eGFP | 0 | 0 | 0 | 0 |
| VVΔB14R-amiR-PolyLFG | 30630.34 | 4551.50 | 69254.90 | 5437.15 |
| VVΔB14R-amiR-MonoLFG | 30720.53 | 4756.02 | 72327.98 | 6198.14 |

TABLE 25

Copy numbers of mature amiR-LacZ were determined by qPCR analysis using specific primers for amiR-LacZ.

|  | MOI 0.1 | | | |
|---|---|---|---|---|
|  | 24 hr | | 48 hr | |
|  | Avg Quant. | SD | Avg Quant. | SD |
| Mock | 0 | 0 | 0 | 0 |
| VVΔB14R | 0 | 0 | 0 | 0 |
| VVΔB14R-amiR-LacZ | 60649.27 | 4977.49 | 94008.16 | 14730.22 |
| VVΔB14R-amiR-Fluc | 0 | 0 | 0 | 0 |
| VVΔB14R-amiR-eGFP | 0 | 0 | 0 | 0 |
| VVΔB14R-amiR-PolyLFG | 100851.02 | 15969.47 | 101159.80 | 11490.84 |
| VVΔB14R-amiR-MonoLFG | 97037.39 | 14400.21 | 104537.41 | 13013.99 |

Extracellular Vesicle-Directing Cassettes Direct Encoded miRNA Hairpins to Extracellular Vesicles One or more of the identified pre-miRNAs may be used to enhance EV secretion of the encoded miRNA hairpin produced by a viral-infected cell by, for example, including in the viral genome a nucleotide sequence that encodes the EV-directing cassettes for that virus. For example, a vesicular stomatitis virus, or variant thereof, whose genome includes a nucleotide sequence that encodes a pre-miRNA having a sequence that includes: SEQ ID NO: 20, sense miRNA sequence [X], SEQ ID NO: 22, anti-sense miRNA sequence [X'], and SEQ ID NO: 21 enhances EV secretion of the encoded miRNA hairpin (made up of sense and anti-sense sequences [X] and [X']) when the virus is used to infect a cell.

In one example, a miRNA hairpin that included GTTGGCACCAGCAGCGCAC (SEQ ID NO: 174) as [X] and GTGCGCTGCTGGTGCCAAC (SEQ ID NO: 175) as [X'], and a loop sequence [Y] according to SEQ ID NO: 163 was cloned into a pre-miRNA that included SEQ ID NOs: 39 and 40, and flanking regions [Z] and [Z'] according to SEQ ID NOs: 18 and 19. Together, the resulting cassette included the sequences: SEQ ID NO: 18, followed by SEQ ID NO: 39, followed by SEQ ID NO: 174, followed by SEQ ID NO: 163, followed by SEQ ID NO: 175, followed by SEQ ID NO: 40, and followed by SEQ ID NO: 19. The RNA sequence of SEQ ID NO: 174 is an shRNA that targets Firefly luciferase (shRNA-luciferase). The cassette was cloned into a VSVΔG virus genome, and the virus was used to infect Vero cells. After 24 hpi (hours post-infection), EVs were isolated by differential centrifugation and the total extracellular vesicular RNA was extracted. qPCR analysis indicates that upon its expression from the pre-miRNA backbone, the shRNA-luciferase hairpin was enriched in the extracellular vesicular fraction by a ratio of over 79,000 to 1 (EVs derived from VSV-shRNA-luciferase infected cells: mock infected cells).

In another example, a sequence that encodes the active stem sequence of hsa-miR-1289-1 (sense sequence [X]: UAAAUGCAGACUCUUGGUUUCCA, SEQ ID NO:176; anti-sense sequence [X']: UGGAGUCCAGGAAUCUG-CAUUUU, SEQ ID NO: 177), and a loop sequence [Y] according to SEQ ID NO: 163 was cloned into a cassette based on miR-30b. The cassette based on miR-30b included SEQ ID NOs: 39 and 40, and flanking regions [Z] and [Z'] according to SEQ ID NOs: 18 and 19. Together, the resulting cassette included the sequences: SEQ ID NO: 18, followed by SEQ ID NO: 39, followed by SEQ ID NO: 176 followed by SEQ ID NO: 163, followed by SEQ ID NO: 177, followed by SEQ ID NO: 40, and followed by SEQ ID NO: 19. The hsa-miR-1289 hairpin is a tumor suppressor miRNA. A Vaccinia virus expressing this cassette was used to infect cells. After 48 hpi, EVs were isolated by differential centrifugation and the total extracellular vesicular RNA was extracted. qPCR analysis indicated that the hsa-miR-1289 was expressed from the pre-miRNA, and enriched in the extracellular vesicular fraction. miR-1289 levels were normalized to 18S and levels of mature miR-1289 in mock infected cells was set as 1. A 52.9 fold increase in EVs miR-1289 levels was measured for VV-miR-1289 infected cells over mock infected cells.

Specific Examples of Cassettes Used for Exosome Delivery During Virus Infection

Tables 2, 3, 4, and 5 identified general cassette sequences based on originating miR stem-loop sequences. Appendix C provides specific examples of cassette sequences that include specific [X] and [X'] sequences. The nucleotide sequences in bold correspond to the [A] and [B] sequences, the underlined nucleotide sequences correspond to the [X] and [X'] sequences, and the nucleotide sequence in italics correspond to the loop sequence [Y]. The specific examples shown in Appendix C do not include [Z] or [Z'] sequences, though alternative examples are envisioned with [Z] and [Z'] sequences.

In the preceding description, for purposes of explanation, numerous details are set forth in order to provide a thorough understanding of the examples. However, it will be apparent to one skilled in the art that these specific details are not required. Accordingly, what has been described is merely illustrative of the application of the described examples and numerous modifications and variations are possible in light of the above teachings.

Since the above description provides examples, it will be appreciated that modifications and variations can be effected to the particular examples by those of skill in the art. Accordingly, the scope of the claims should not be limited by the particular examples set forth herein, but should be construed in a manner consistent with the specification as a whole.

---
APPENDIX A
---

Cassette sequence amiR1
(SEQ ID NO: 178)
GAAGGTATATTGCTGTTGACAGTGAGCGATAGGAGAAGAGACATGTTGGTTAGTGAAGCCACAGATGTAATAGGAGAAGAGACATGTTGGTTGCCTACTGCCTCGG Cassette sequence amiR2
(SEQ ID NO: 179)
GAAGGTATATTGCTGTTGACAGTGAGCGTTGTCTTATTCTTTAATAACATTAGTGAAGCCACAGATGTAATGTTATTAAAGAATAAGACAATGCCTACTGCCTCGG Cassette sequence amiR3
(SEQ ID NO: 180)
GAAGGTATATTGCTGTTGACAGTGAGCGTTGTCTTACTCTTCAATAACATTAGTGAAGCCACAGATGTAACCAACATGTCTCTTCTCCTATTGCCTACTGCCTCGG Cassette sequence amiR5
(SEQ ID NO: 181)
GAAGGTATATTGCTGTTGACAGTGAGCGTAGTGATAACTCATAGTACATAGTGAAGCCACAGATGTATGTACTATGAGTTATCACTATGCCTACTGCCTCGG Cassette sequence amiR6
(SEQ ID NO: 182)
GAAGGTATATTGCTGTTGACAGTGAGCGCCGCCATGTCTGTTACGTTAATAGTGAAGCCACAGATGTATTAACGTAACAGACATGGCGG-TGCCTACTGCCTCGG Cassette sequence amiR8
(SEQ ID NO: 183)
GAAGGTATATTGCTGTTGACAGTGAGCGCGCAGAGAGTGTTATATTGCATTAGTGAAGCCACAGATGTAATGCAATATAACACTCTCTGCGTGCCTACTGCCTCGG Cassette sequence amiR9
(SEQ ID NO: 184)
GAAGGTATATTGCTGTTGACAGTGAGCGAGGAATTAAGGTAGAGGTTATATAGTGAAGCCACAGATGTATATAACCTCTACCTTAATTCCTTGCCTACTGCCTCGG Cassette sequence amiR10
(SEQ ID NO: 185)
GAAGGTATATTGCTGTTGACAGTGAGCGAGGCAGAGAAGGGTATGGAATTAGTGAAGCCACAGATGTAATTCCATACCCTTCTCTGCCTTGCCTACTGCCTCGG

---
APPENDIX B
--- miR-Cassette sequence shRNA-BRCA1(h/m):
(SEQ ID NO: 186)
CTTGGGAATGGCAAGGCACAAAGTGTGACCACATATTTATGTGGTCACACTTTGTATCTTGCTATACCCAGAAA miR-Cassette sequence shRNA-BRCA2(h/m):
(SEQ ID NO: 187)
CTTGGGAATGGCAAGGTACAGGATATGCGAATTAAGAATAATTCGCATATCCTGTCTCTTGCTATACCCA miR-Cassette sequence shRNA-BRCA2(h):
(SEQ ID NO: 188)
GAAGGTATATTGCTGTTGACAGTGAGCGAAAGAACAATATCCTACTAGTTTAGTGAAGCCACAGATGTAAACTAGTAGGATATTGTTCTTCTGCCTACTGCCTCGG miR-Cassette sequence shRNA-PDL1(m):
(SEQ ID NO: 189)
CTTGGGAATGGCAAGGTTCAACACTGCTTACGTCTCCTGACGTAAGCAGTGTTGACTCTTGCTATACCCAGAAA miR-Cassette sequence shRNA-Luciferase:
(SEQ ID NO: 190)
GAAGGTATATTGCTGTTGACAGTGAGCGCACGCTGGGCGTTAATCAAAGACTGTGAAGCCACAGATGGGTCTTTGATTAACGCCCAGCGTTTGCCTACTGCCTCGGACTTCAAGGGGCTACTTTAGG miR-Cassette sequence shRNA-eGFP:
(SEQ ID NO: 191)
GAAGGTATATTGCTGTTGACAGTGAGCGCACGTCTATATCATGGCCGACACTGTGAAGCCACAGATGGGTGTCGGCCATGATATAGACGTTTGCCTACTGCCTCGGACTTCAAGGGGCTACTTTAGG miR-Cassette sequence shRNA-BGal:
(SEQ ID NO: 192)
GAAGGTATATTGCTGTTGACAGTGAGCGCACGTGACCTATCCCATTACGGCTGTGAAGCCACAGATGGGCCGTAATGGGATAGGTCACGTTTGCCTACTGCCTCGGACTTCAAGGGGCTACTTTAGG

---
APPENDIX C
--- hsa-miR-484 as originating miR stem-loop sequence (i.e. [A] and [B] correspond to SEQ ID Nos: 84 and 85, respectively).
Underlined [X] and [X'] sequences correspond to an exemplary shRNA-PDL1 sequence (to target mouse PDL1)
(SEQ ID NO: 193)
AGCCUCGUUCAACACUGCUUACGUCUCCUAAACCCCUAAAUAGGGACUUUCAG

AGAUGUCAGCUUGAGCUUUUUUGGCG

APPENDIX C

Underlined [X] and [X'] sequences correspond to an exemplary shRNA-BRCA2 sequence (to target mouse and human BRCA2)
(SEQ ID NO: 194)
AGCCUCG<u>ACAGGAUAUGCGAAUUAAGAA</u>*AAACCCCUAAAUAGGGACUUU*<u>CCC</u>

<u>UUACUUUGCACUGUG</u>CUUUUUUGGCG

Underlined [X] and [X'] sequences correspond to an exemplary variant of amiR-6
(SEQ ID NO: 195)
AGCCUCG<u>ACCGUCAUGUCUGUUACGUUAA</u>*AAACCCCUAAAUAGGGACUUU*<u>CCA</u>

<u>ACGCAAUAGAACGGG</u>CUUUUUUGGCG hsa-miR-143 as originating miR stem-loop sequence (i.e. [A] and [B] correspond to SEQ ID Nos: 20 and 21, respectively).
Underlined [X] and [X'] sequences correspond to an exemplary shRNA-PDL1 sequence (to target mouse PDL1)
(SEQ ID NO: 196)
GCGCAGCGCCCUGUCUCCCAGCCU<u>AAGAUGUGACGAAGGCAGAGCGGU</u>*CAGUU*

*GGGAGU*<u>CCCUCUGCAUUCGUCACAACUU</u>AGGAAGAGAGAAGUUGUUCUGCAGC

Underlined [X] and [X'] sequences correspond to an exemplary shRNA-BRCA2 sequence (to target mouse and human BRCA2)
(SEQ ID NO: 197)
GCGCAGCGCCCUGUCUCCCAGCCU<u>AUGACCUAUACGCGUAAUUCAGGU</u>*CAGUU*

*GGGAGU*<u>CAGAAUUAAGCGUAUAGGACAU</u>AGGAAGAGAGAAGUUGUUCUGCAGC

Underlined [X] and [X'] sequences correspond to an exemplary variant of amiR-6
(SEQ ID NO: 198)
GCGCAGCGCCCUGUCUCCCAGCCU<u>UGGGAGUACAGACGAUGCAAAGGU</u>*CAGUU*

*GGGAGU*<u>CAUUGCAUUGUCUGUACUGCCA</u>AGGAAGAGAGAAGUUGUUCUGCAGC hsa-miR-99a as originating miR stem-loop sequence (i.e. [A] corresponds to SEQ ID No: 23; and [B] corresponds to a variant of SEQ ID NO: 24).
Underlined [X] and X'] sequences correspond to an exemplary shRNA-PDL1 sequence (to target mouse PDL1)
(SEQ ID NO: 199)
CCCAUUGGCAUA<u>UUCAACACCUGCUUACGUCUUCCU</u>*GUGAAGUGGACCG*<u>AGG</u>

<u>AGAUGUAUCCAGUGUUGAC</u>UGUGUCAGUGU

Underlined [X] and [X'] sequences correspond to an exemplary shRNA-BRCA2 sequence (to target mouse and human BRCA2)
(SEQ ID NO: 200)
CCCAUUGGCAUA<u>UACAGGAUAUGCGAAUUAAGAA</u>*GUGAAGUGGACCG*<u>UUCUU</u>

<u>AGUUCCGAUAUCCUGUCAG</u>UGUGUCAGUGU

Underlined [X] and [X'] sequences correspond to an exemplary variant of amiR-6
(SEQ ID NO: 201)
CCCAUUGGCAUA<u>ACCGUCAUGUCUGUUACGUUAA</u>*GUGAAGUGGACCG*<u>UUAAC</u>

<u>GGAACUCACAUGACGGCAG</u>UGUGUCAGUGU hsa-miR-181c as originating miR stem-loop sequence (i.e. [A] corresponds to SEQ ID No: 87 with two additional nucleotides; and [B] corresponds to SEQ ID NO: 88).
Underlined [X] and [X'] sequences correspond to an exemplary shRNA-PDL1 sequence (to target mouse PDL1)
(SEQ ID NO: 202)
CGGAAAAUUUGCCAAGGGUUUGGGGG<u>UUCAACACUGCUUACGUCUCCU</u>*UUGG*

*GCAGCUCAGGCAA*<u>AGAGACGUACCAGUGUUGGU</u>CCUGAGGCCUGGAAUUGCC

AUCCU

(SEQ ID NO: 203)
Underlined [X] and [X'] sequences correspond to an exemplary shRNA-BRCA2 sequence (to target mouse and human BRCA2)
CGGAAAAUUUGCCAAGGGUUUGGGGG<u>UACAGGAUAUGCGAAUUAAGAA</u>*UUGG*

*GCAGCUCAGGCAA*<u>UUUUAAUUCUAUAUCCUGGU</u>CCUGAGGCCUGGAAUUGCC

AUCCU

APPENDIX C

Underlined [X] and [X'] sequences correspond to an exemplary variant of amiR-6
(SEQ ID NO: 204)

CGGAAAAUUUGCCAAGGGUUUGGGGGACCGUCAUGUCUGUUACGUUAA*UUGG*

*GCAGCUCAGGCA*AUUACGUAACCACAUGACGUA*CCUGAGGCCUGGAAUUGCC*

AUCCU hsa-miR-199a1 as originating miR stem-loop sequence (i.e. [A] corresponds to SEQ
ID No: 93 with two additional nucleotides; and [B] corresponds to SEQ ID NO: 94).
    Underlined [X] and [X'] sequences correspond to an exemplary shRNA-PDL1
    sequence (to target mouse PDL1)
(SEQ ID NO: 205)

GCCAAUGGCAUCUCGGCUAGAACCACUC*AGGAGGCUCUCAAUGUGU*GUGUUC

UAGCCUAGAUGCCCAAGGC

Underlined [X] and [X'] sequences correspond to an exemplary shRNA-BRCA2
sequence (to target mouse and human BRCA2)
(SEQ ID NO: 206)

GCCAAUUCCUAUAUGCUUAAUUCCUUUC*AGGAGGCUCUCAAUGUGU*AAGAAU

UAAGCGUAUAGGACAAGGC

Underlined [X] and [X'] sequences correspond to an exemplary variant of amiR-6
(SEQ ID NO: 207)

GCCAAUCAGUACAUACAAUGCACAUUUC*AGGAGGCUCUCAAUGUGU*AAUUGCA

UUGUCUGUACUGCCAGGC

---

What is claimed is:

1. A cassette encoded by a virus that, when processed by a cell that is infected by the virus, increases extracellular vesicle secretion of at least one miRNA hairpin encoded by the cassette, wherein:

the cassette includes at least one sequence according to: [Z]-[A]-[X]-[Y]-[X']-[B]-[Z'], wherein:

[Z]-[Z'] are optional and, when present, represent sequences according to SEQ ID NOs: 18 and 19, respectively;

[A] and [B] represent sequence according to SEQ ID NOs: 27 and 28, respectively;

[X] and [X'] represent sequences according to SEQ ID NOs: 1 and 2, 3 and 4, 5 and 6, 7 and 8, 9 and 10, 11 and 12, 13 and 14, or 15 and 16, respectively; and

[Y] represents a sequence according to SEQ ID NO: 17 or 29.

2. A virus whose genome comprises a nucleotide sequence that encodes one or more cassettes according to claim 1.

* * * * *